US006845776B2

(12) United States Patent
Stack et al.

(10) Patent No.: US 6,845,776 B2
(45) Date of Patent: *Jan. 25, 2005

(54) SATIATION DEVICES AND METHODS

(76) Inventors: Richard S. Stack, 106 Alder Pl., Chapel Hill, NC (US) 27514; Richard A. Glenn, 308 W. side Dr., Chapel Hill, NC (US) 27516; William L. Athas, 3901 King Charles Rd., Durham, NC (US) 27707; Michael S. Williams, 6909 Erland Rd., Santa Rosa, CA (US) 95404

(*) Notice: Subject to any disclaimer, the term of this patent is extended or adjusted under 35 U.S.C. 154(b) by 75 days.

This patent is subject to a terminal disclaimer.

(21) Appl. No.: 10/118,289

(22) Filed: Apr. 8, 2002

(65) Prior Publication Data

US 2003/0040808 A1 Feb. 27, 2003

Related U.S. Application Data

(63) Continuation-in-part of application No. 09/940,110, filed on Aug. 27, 2001, now Pat. No. 6,675,809.

(51) Int. Cl.[7] ............................. A61B 19/00; A61F 2/04
(52) U.S. Cl. .................................... 128/898; 623/23.65
(58) Field of Search .............................. 623/1.1, 11.11, 623/23.64, 23.65; 600/37; 606/213–217, 139, 192

(56) References Cited

U.S. PATENT DOCUMENTS

| 4,246,893 A | 1/1981 | Berson ........................ 128/1 R |
| 4,315,509 A | 2/1982 | Smit ....................... 128/303 R |
| 4,403,604 A | 9/1983 | Wilkinson et al. .......... 128/1 R |
| 4,416,267 A | 11/1983 | Garren et al. ............... 128/1 R |
| 4,607,618 A | 8/1986 | Angelchik .................. 128/1 R |
| 4,641,653 A | 2/1987 | Rockey ....................... 128/344 |

(List continued on next page.)

FOREIGN PATENT DOCUMENTS

| WO | WO 91/01117 | 2/1991 | |
| WO | WO 00/12027 | 3/2000 | ............. A61F/2/04 |
| WO | WO 00/32137 | 6/2000 | ............. A61F/2/04 |
| WO | WO 01/49359 | 7/2001 | .......... A61M/31/00 |

*Primary Examiner*—David J. Isabella
(74) *Attorney, Agent, or Firm*—Stallman & Pollock LLP

(57) ABSTRACT

A device for inducing weight loss in a patient includes a tubular prosthesis positionable at the gastro-esophageal junction region, preferably below the z-line. In a method for inducing weight loss, the prosthesis is placed such that an opening at its proximal end receives masticated food from the esophagus, and such that the masticated food passes through the pouch and into the stomach via an opening in its distal end.

27 Claims, 22 Drawing Sheets

U.S. PATENT DOCUMENTS

| | | | |
|---|---|---|---|
| 4,648,383 A | 3/1987 | Angelchik | 128/1 R |
| 4,694,827 A | 9/1987 | Weiner et al. | 128/303 R |
| 4,723,547 A | 2/1988 | Kullas et al. | 128/329 R |
| 4,846,836 A | 7/1989 | Reich | 623/11 |
| 4,899,747 A | 2/1990 | Garren et al. | 606/192 |
| 5,234,454 A | 8/1993 | Bangs | 606/191 |
| 5,246,456 A | 9/1993 | Wilkinson | 623/12 |
| 5,259,399 A | 11/1993 | Brown | 128/897 |
| 5,290,217 A * | 3/1994 | Campos | 600/37 |
| 5,306,300 A | 4/1994 | Berry | 623/11 |
| 5,314,473 A | 5/1994 | Godin | 623/12 |
| 5,327,914 A | 7/1994 | Shlain | 128/898 |
| 5,345,949 A | 9/1994 | Shlain | 128/898 |
| 5,514,176 A | 5/1996 | Bosley, Jr. | 623/1 |
| 5,593,434 A | 1/1997 | Williams | 623/1 |
| 5,653,743 A | 8/1997 | Martin | 623/1 |
| 5,662,713 A | 9/1997 | Andersen et al. | 623/12 |
| 5,674,241 A | 10/1997 | Bley et al. | 606/198 |
| 5,720,776 A | 2/1998 | Chuter et al. | 623/1 |
| 5,771,903 A | 6/1998 | Jakobsson | 128/898 |
| 5,820,584 A | 10/1998 | Crabb | 604/49 |
| 5,861,036 A | 1/1999 | Godin | 623/12 |
| 5,868,141 A | 2/1999 | Ellias | 128/898 |
| 5,887,594 A | 3/1999 | LoCicero, III | 128/898 |
| 5,922,019 A | 7/1999 | Hankh et al. | 623/1 |
| 5,993,483 A | 11/1999 | Gianotti | 623/1 |
| 6,102,922 A | 8/2000 | Jakobsson et al. | 606/157 |
| 6,113,609 A | 9/2000 | Adams | 606/139 |
| 6,146,416 A | 11/2000 | Andersen et al. | 623/1.15 |
| 6,254,642 B1 | 7/2001 | Taylor | 623/23.64 |
| 6,264,700 B1 | 7/2001 | Kilcoyne et al. | 623/23.68 |
| 6,302,917 B1 | 10/2001 | Dua et al. | 623/23.68 |
| 6,503,264 B1 * | 1/2003 | Birk | 606/191 |
| 6,540,789 B1 | 4/2003 | Silverman et al. | 623/23.65 |
| 6,547,801 B1 | 4/2003 | Dargent et al. | 606/157 |
| 6,558,400 B2 * | 5/2003 | Deem et al. | 606/151 |
| 6,572,627 B2 | 6/2003 | Gabbay | 606/151 |
| 6,663,639 B1 * | 12/2003 | Laufer et al. | 606/139 |
| 2001/0011543 A1 | 8/2001 | Forsell | 128/899 |
| 2001/0020189 A1 | 9/2001 | Taylor | 623/23.68 |
| 2001/0020190 A1 | 9/2001 | Taylor | 623/23.68 |
| 2002/0022851 A1 | 2/2002 | Kalloo et al. | 606/151 |
| 2002/0055757 A1 | 5/2002 | Torre et al. | 606/192 |
| 2002/0183768 A1 | 12/2002 | Deem et al. | 606/151 |

* cited by examiner

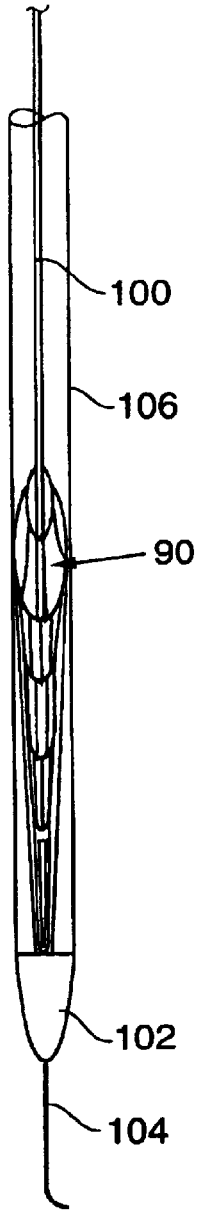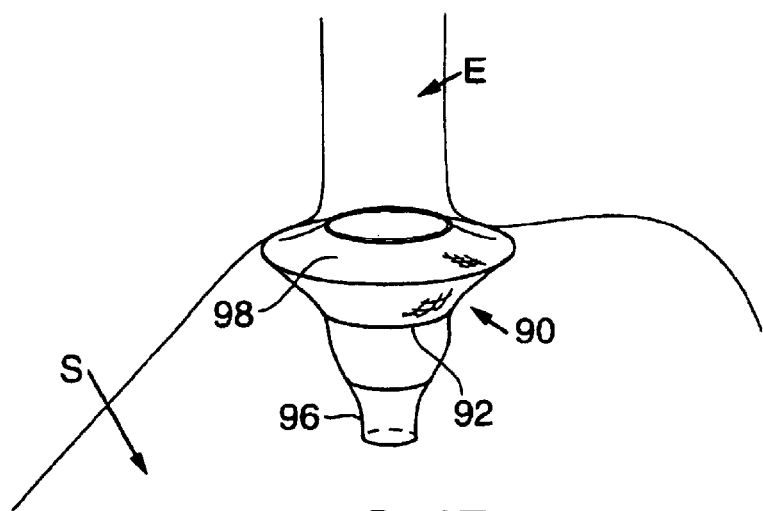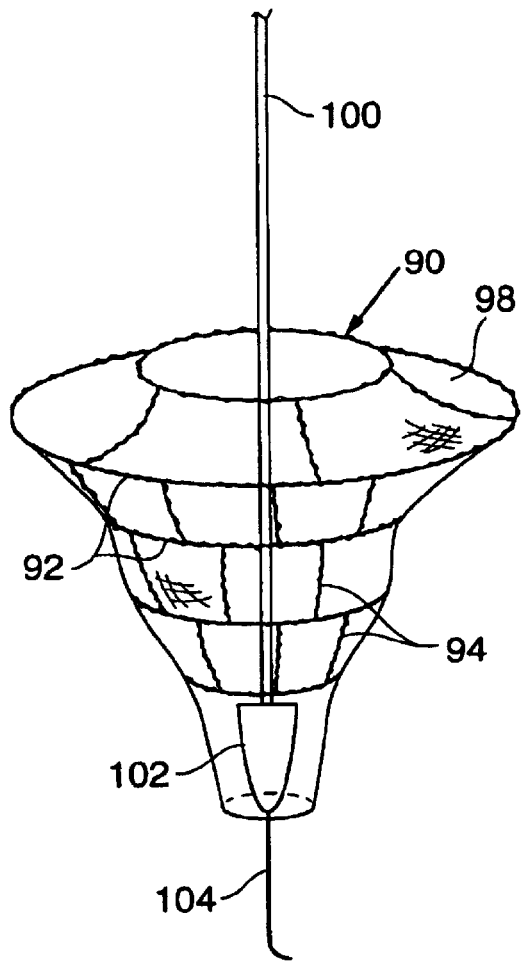
FIG. 17
FIG. 18A
FIG. 18B

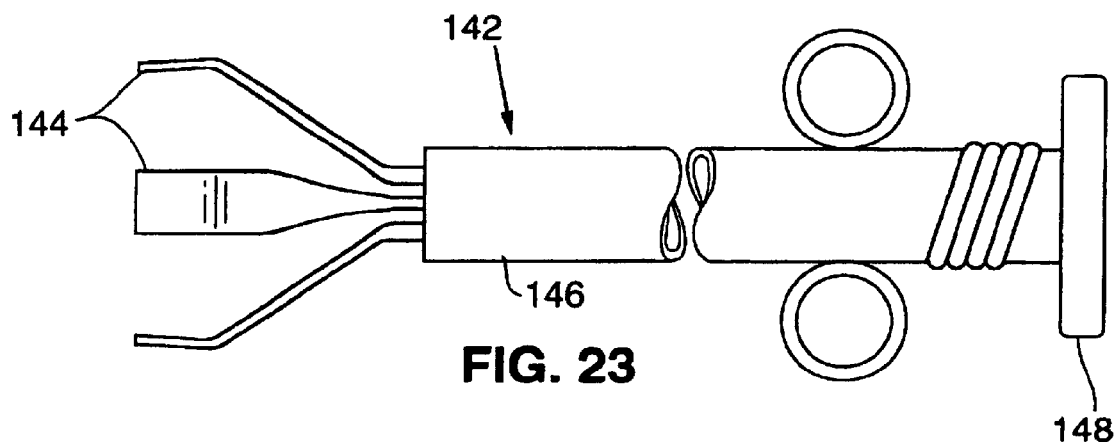
FIG. 23
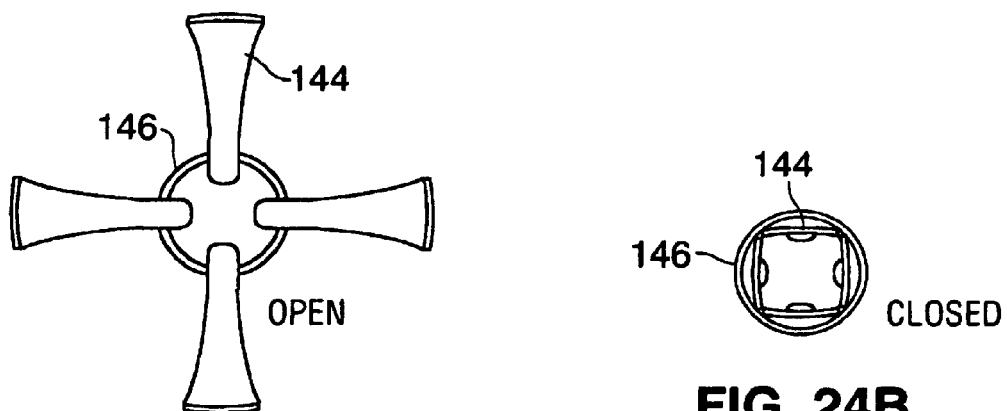
FIG. 24A   FIG. 24B
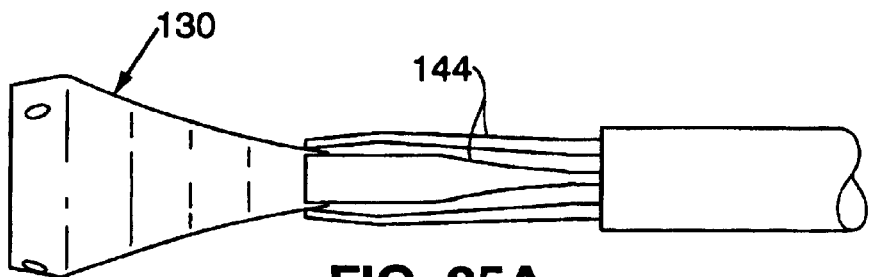
FIG. 25A
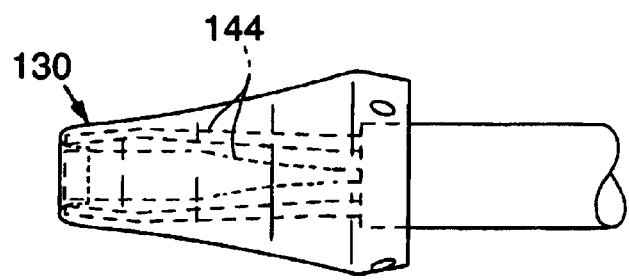
FIG. 25B

SATIATION DEVICES AND METHODS

This application is a cip of U.S. application Ser. No. 09/940,110, filed Aug. 27, 2001 now U.S. Pat. No. 6,675,809.

FIELD OF THE INVENTION

The present invention relates generally to the field of devices and methods for achieving weight loss in humans, and specifically to the use of devices implantable within the human stomach for controlling feelings of hunger.

BACKGROUND OF THE INVENTION

Various medical approaches are used for controlling obesity. These approaches include diet, medication, and surgical procedures. One of the more successful surgical procedures is the vertical banded gastroplexy or the proximal gastric pouch with a Roux-en-Y anastomosis that shunts food from the proximal region of the stomach into the intestine, thereby minimizing absorption of food into the bloodstream. However, known complications are present with each of these procedures and more successful options are desired.

Other alternatives include implantation of gastric balloons that prevent overeating by occupying volume within the stomach. Unfortunately, gastric balloons can migrate down the GI tract, causing obstruction and thus necessitating removal.

It is therefore desirable to provide a successful and minimally-invasive alternative to existing approaches for controlling obesity.

SUMMARY OF THE INVENTION

A satiation device utilizing principles of the present invention includes a tubular pouch positionable at the gastro-esophageal junction. The pouch has a proximal opening for receiving ingested food from the esophagus, and a distal opening for releasing food from the pouch into the stomach. The pouch is proportioned such that release of food from the pouch in to the stomach occurs relatively slowly, causing food to accumulate within the pouch so as to give the patient the sensation of fullness.

BRIEF DESCRIPTION OF THE DRAWINGS

FIGS. 13A and 13B are a schematic illustrations showing use of a coaxial plication device, in which FIG. 13A shows positioning of the catheter after the ring has been positioned and FIG. 13B shows formation of the plication and placement of the locking ring.

FIG. 17 illustrates in vivo positioning of an alternative stomach pouch.

FIG. 18A is a perspective view of the stomach pouch of FIG. 17 within a positioning sheath used for delivery.

FIG. 18B is a perspective view of the stomach pouch of FIG. 17 during deployment. The pouch is shown released from the positioning sheath but still coupled to the mandrel.

FIG. 23 is an alternative delivery device that may be used to deliver a stomach pouch.

FIGS. 24A and 24B are end views of the delivery device of FIG. 23, showing the claws in the opened and closed positions, respectively.

FIGS. 25A and 25B are a sequence of side elevation views showing engagement of a satiation device by the delivery device prior to implantation using the delivery device.

DETAILED DESCRIPTION

Figure 1:
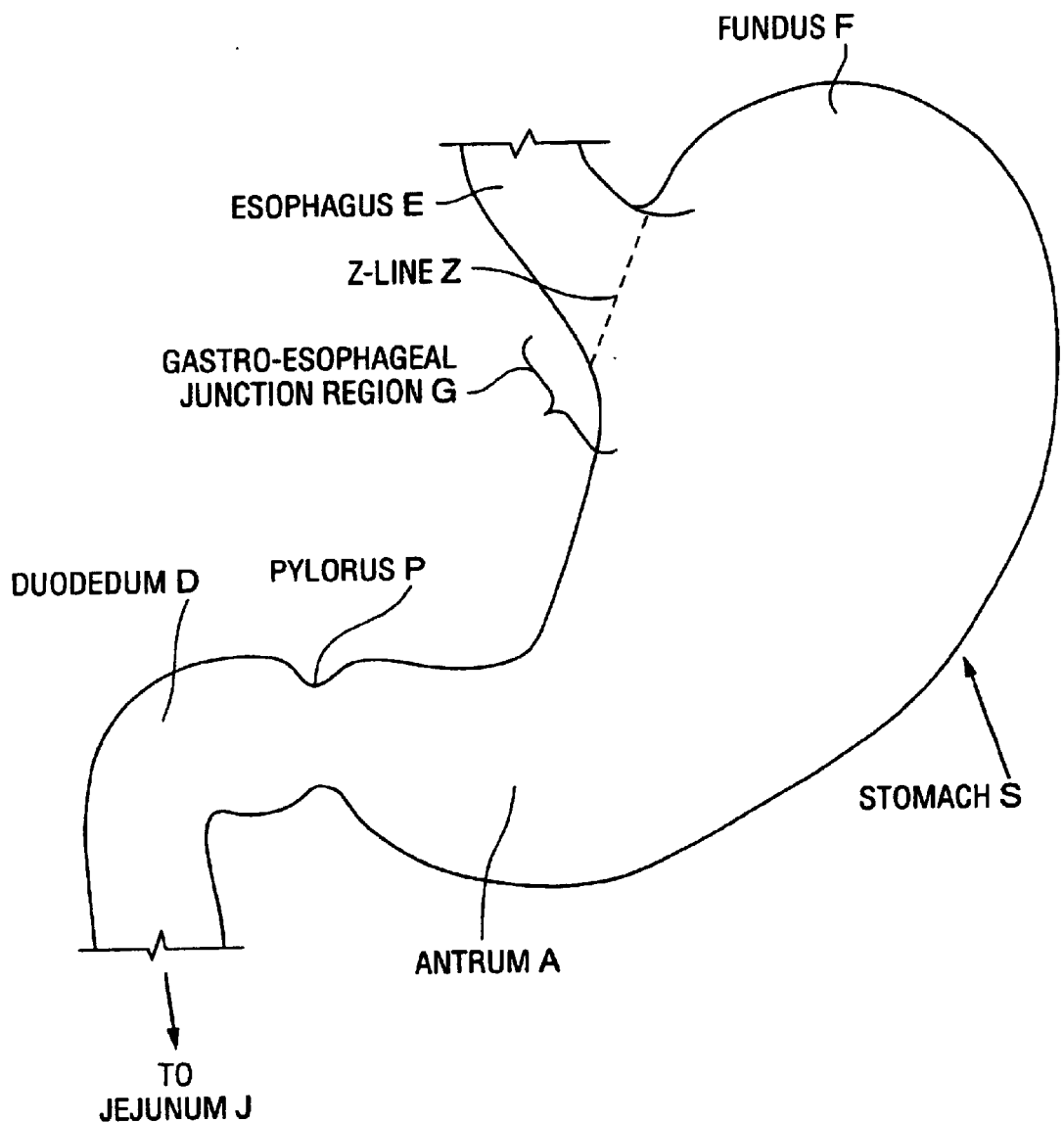
FIG. 1 is a schematic illustration of a human stomach and a portion of the small intestine.

An anatomical view of a human stomach S and associated features is shown in FIG. 1. The esophagus E delivers food from the mouth to the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Various embodiments of satiation devices are described herein. Many of these devices include a pouch or funnel positioned at the gastro-esophageal junction region so as to form a small reservoir which collects masticated food from the esophagus—thereby limiting the amount of food that can be consumed at one time. Over time the food within this reservoir descends into the stomach through a distal opening in the pouch. The pouch may optionally include a tubular extension positionable within the esophagus to facilitate flow of food from the esophagus into the pouch.

Materials that may be used for the pouch include flexible materials that will prevent passage of food through the sides of the pouch. Examples of such materials include, but are not limited to polyesters (e.g. Dacron® polyester), ePTFE fabric (e.g. GoreTex® fabric or others), a polyurethane such as ChronoFlex® polyurethane, nylon fabrics, silicone, other polymeric materials, and bio-absorbable materials (e.g. PLLA, PGA, PCL, poly-amhydride etc). The pouch 12 may be formed of a composite of compliant, semi-compliant and/or non-compliant materials which give different regions of the pouch different degrees of compliance so as to allow/limit expansion of the pouch in various locations. For example, it may be desirable to provide the pouch with a fairly elastic exit port to as to prevent occlusion in the event a large piece of food is ingested, whereas the proximal end of the pouch may be stiffer to prevent bulging. Varying degrees of compliance may also be built into the pouch by varying the cross-sectional thickness of the pouch in different regions of the pouch. The pouch material may be coated with a lubricious, bio-compatible, chemically inert material, such as paraleyne, to reduce friction on the base.

The flexible pouch material may be carried by a supporting structure, such as a soft mesh, coil, a cage structure, ribs, rings etc. The supporting structure may be formed of stainless steel, polymer, shape memory materials (such as nitinol, shape memory alloys, or shape memory polymers), bio-absorbable materials or, in the case of a silicone pouch, thickened regions of silicone. The supporting structure may be located at the interior or exterior of the flexible pouch material. It may be molded into or sewn to the pouch material, or it may be attached using a suitable adhesive. If a tightly woven mesh or tightly wound coil is provided, the flexible pouch material may be eliminated. Alternatively, a mesh may be provided having a polymeric material embedded in the interstices of the mesh, in which case a separate internal or external covering of pouch material may be eliminated.

The pouch is preferably constructed so as to be self-expanding, such that the pouch springs radially open into an expanded condition upon ejection from a deployment device or catheter as more fully described below.

In many of the embodiments, the pouch is formed to have a funnel shape. However, a variety of alternative shapes may be used for the pouch. For example, the pouch may have a much shorter proximal-to-distal dimension and thus take the shape of a shallow saucer with a small hole on its bottom surface. Other examples include, but are not limited to, egg shapes, other tapered shapes such as the shape of a "spinning top", cylindrical shapes, and other symmetrical or asymmetrical shapes.

The device may be modular in that where multiple components are to be implanted, the various components may be provided separately from one another. In such a modular system, the separately implanted components may be attached to one another within the body during implantation, or certain ones of them may remain unattached to one another even after implantation. Alternatively, the physician may assemble the components to one another just prior to implantation. Modular components are desirable in that they permit the physician to select sizes for each component that are appropriate for the patient.

Figure 2:
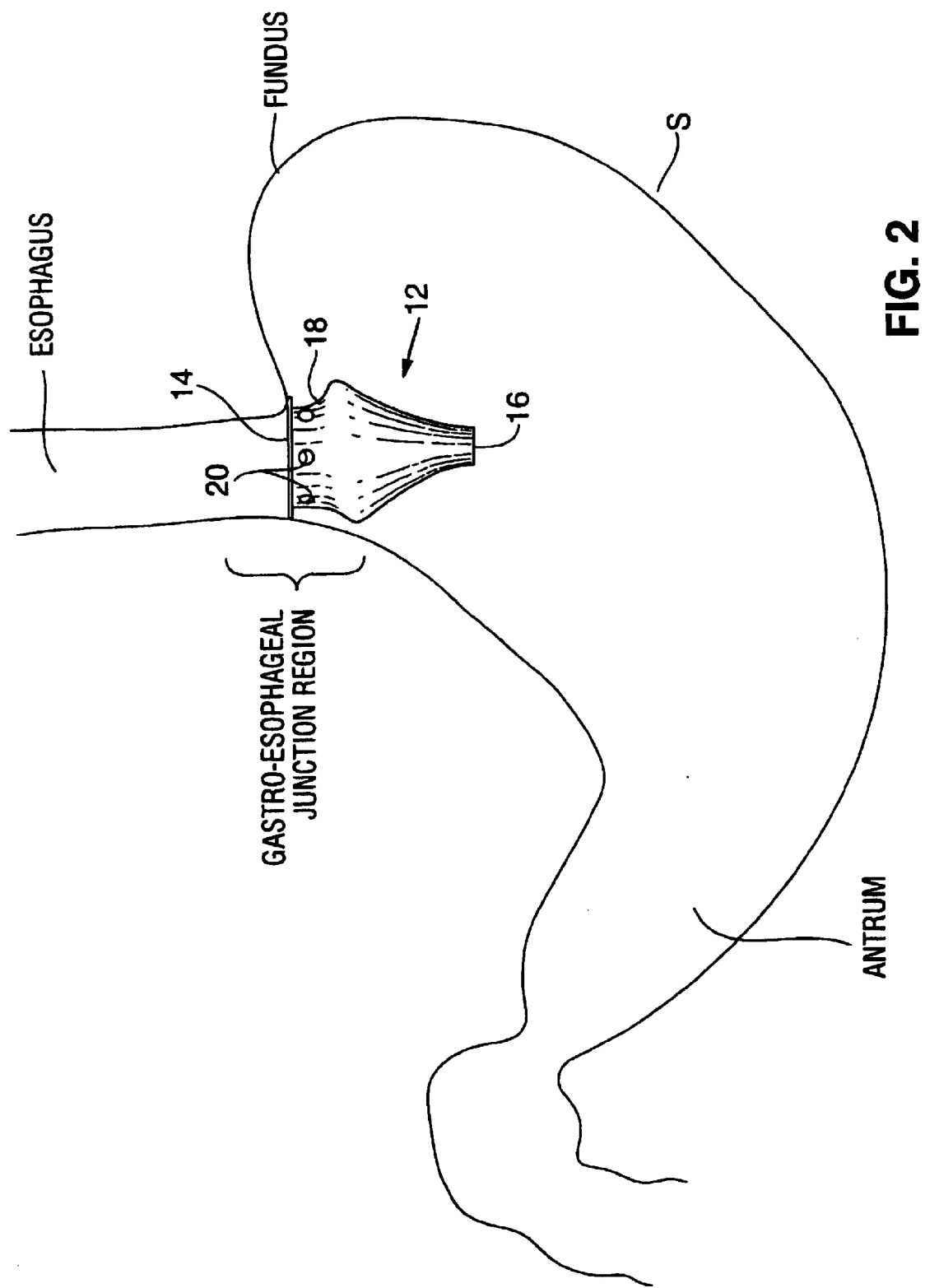
FIG. 2 is a schematic illustration similar to FIG. 1 showing in vivo positioning of a stomach pouch.

One embodiment of a satiation device is illustrated in FIG. 2 and includes a pouch 12 that is positioned in the proximal region of the stomach. Pouch 12 includes a proximal opening 14 that is positionable at the gastro-esophageal junction region (and preferably below the z-line) as shown, and a distal opening 16 that opens into the interior of the stomach S. In this embodiment, the pouch 12 tapers outwardly from the proximal opening to form an apron 18, and then tapers inwardly towards the distal opening 16 to give the distal portion of the pouch 12 a funnel shape. However, a variety of alternative shapes may be used for the pouch. For example, the pouch may have a much shorter proximal-to-distal dimension and thus take the shape of a shallow saucer with a small hole on its bottom surface.

Because of its small volume (which may be on the order of approximately 2 cc–300 cc in volume, but is preferably in the range of 10–30 cc), the pouch functions to limit the amount of food that can be consumed at one time.

Pouch 12 may be formed of a flexible material that will prevent passage of food through the sides of the pouch, such as Dacron® polyester, silicone, or other polymeric material. The pouch 12 may be formed of a composite of compliant, semi-compliant and/or non-compliant materials which give different regions of the pouch different degrees of compliance. Such a composite would allow/limit expansion of the pouch in various locations, so as to help control the passage rate of food material through the pouch and/or the exit pressure of the food from the pouch. If silicone is used, varying degrees of compliance may be built into the pouch by varying the cross-sectional thickness of the pouch in different regions of the pouch. The pouch material may be coated with a lubricious, bio-compatible, chemically inert material, such as paraleyne, to reduce friction on the base material's surface which will help prevent sticking and food build up on the device.

During implantation the pouch 12 is secured at the gastro-esophageal junction region G using sutures, clips, adhesives or other suitable means. Although the pouch may be secured to the esophageal tissue, it is more preferable to apply sutures/clips below the Z-line to allow for attachment to the thicker tissue of the stomach wall. Suture attachment points, which may take the form of holes, eyelets or grommets 20 in the pouch may be used to provide reinforced regions for anchoring the sutures. Although as few or as many of such suture/clip attachment points as needed may be used, at least four such points are desirable, such as at 90° intervals around the pouch, so as to enable the pouch to be secured around the full circumference of the tissue. The suture attachment points may be made of a suitably dense radio-opaque material, such as titanium or gold, to add in visualization of the device during or after the procedure. Each suture attachment point may also be marked using a different color to facilitate identification and orientation of sutures. If the pouch is formed of silicone, the proximal portion of the pouch (in which the eyelets 20 are located) may be formed of more durable material such as a woven material, Dacron® polyester or ePTFE fabric in lieu of silicone so as to provide a more durable sewing region. Although grommets, eyelets or reinforced regions may be advantageous, the pouch may alternatively be provided without suture attachment points formed of special materials (with or without identifying markings)—in which case the sutures are passed directly through the pouch material.

The flexible pouch material may be carried by supporting members, such as a soft mesh, a cage structure, ribs, rings etc. The supporting members may be formed of stainless steel, polymer, shape memory materials such as nitinol, shape memory alloys, or shape memory polymers, or thickened regions of pouch material. The pouch is preferably constructed so as to be self-expanding, such that the pouch springs radially open into an expanded condition upon ejection from a deployment device or catheter as more fully described below.

Figure 3:
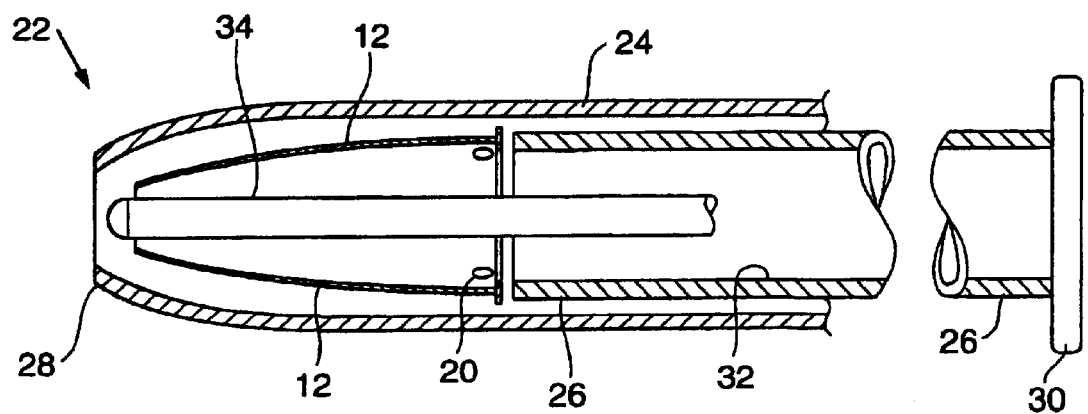
FIG. 3 is a cross-sectional side elevation view of a delivery system which may be used to deliver a satiation device such as the pouch of FIG. 2.

FIG. 3 shows a delivery system 22 of a type that may be used to implant the pouch 12 as well as any of the other satiation devices described herein. Delivery system 22 includes an elongate tubular sheath 24 and a pusher tube 26 slidably received within the sheath. Sheath 24 includes a distal end 28 that is slightly tapered and formed of a flexible material such as a low durometer polyethylene so as to minimize trauma to body tissues contacted by the end 28 during its movement into and within the esophagus and stomach.

Figure 4A:
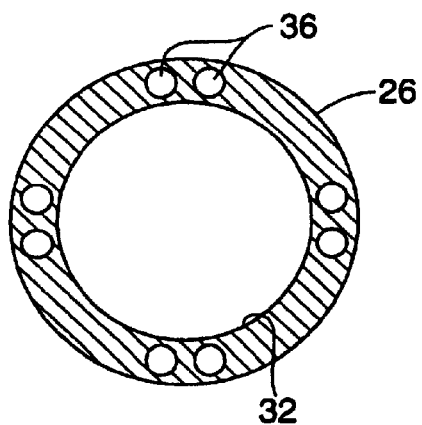
FIG. 4A is a cross-sectional end view of the pusher tube of the delivery system of FIG. 3.
Figure 4B:
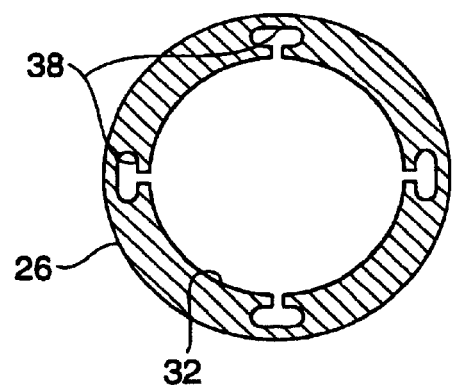
FIG. 4B is an alternative cross-sectional end view of a pusher tube that may be used for the delivery system of FIG. 3.

Pusher tube 26 is an elongate tube extending through the sheath 24 and extending slightly from the proximal end of the sheath 24. A handle 30 may be formed at the proximal end of the pusher tube 26 to facilitate movement of the pusher tube relative to the sheath 24. Pusher tube 26 includes a central lumen 32 for receiving devices that may be needed at the implantation site. Such devices may include, for example, an endoscope 34 to provide visualization of the implant procedure, or other devices if needed to ensure proper placement of the implant. A plurality of circumferential lumen 36 (FIG. 4A) and/or grooves 38 (FIG. 4B) are positioned circumferentially in the pusher tube 26. During use, suture strands may be positioned within these lumen/grooves so as to keep the strands separated from one another.

Figure 5:
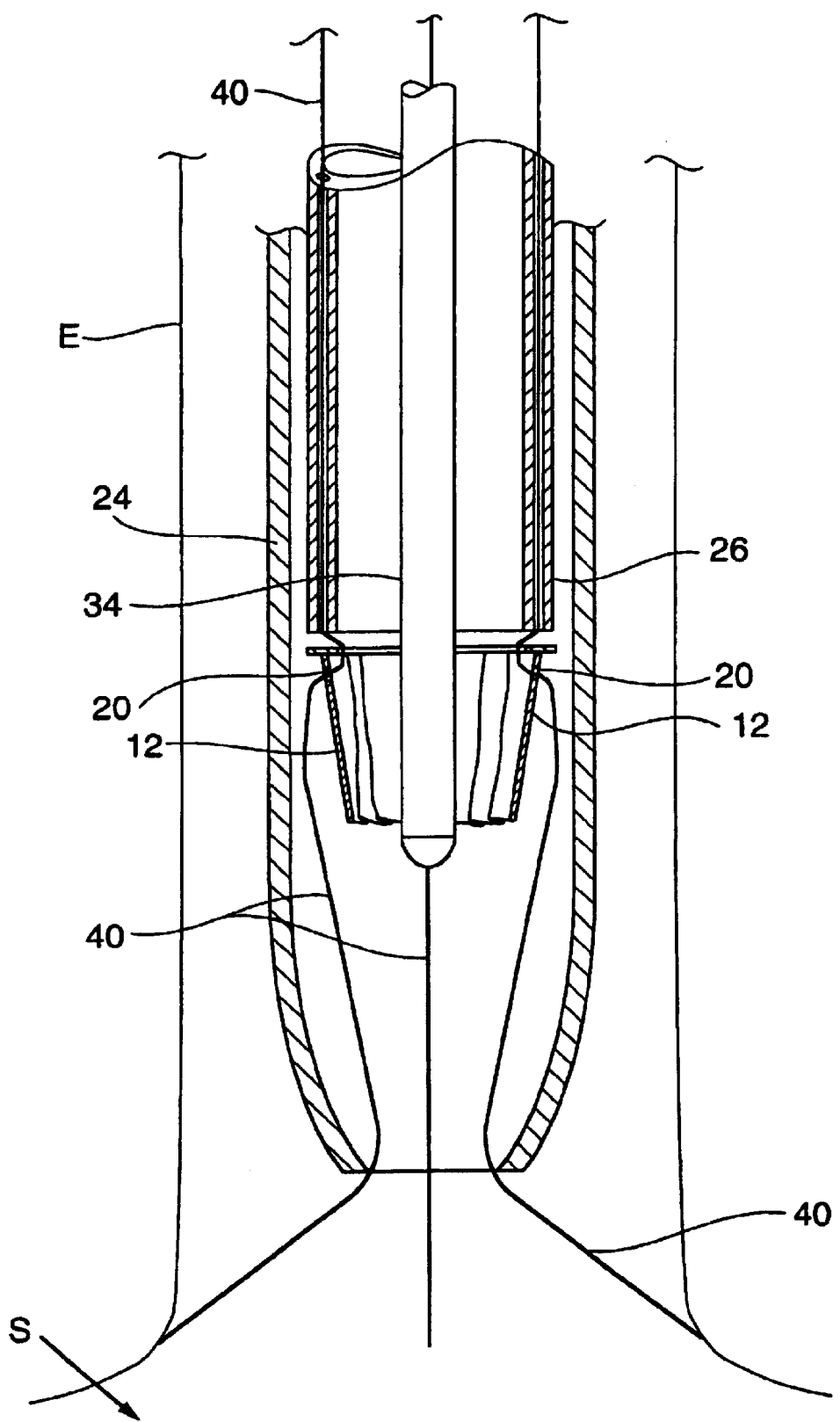
FIG. 5 is a cross-sectional side elevation view of the delivery system of FIG. 3 during delivery of a pouch into the gastro-esophageal junction.

Referring to FIG. 5, in preparation for implantation of pouch 12, suture strands 40 are secured to the eyelets 20 of the pouch, and the pouch is folded or rolled and placed in the distal end of sheath 24. A proximal end of each suture strand is drawn out the proximal end of the sheath 24 and threaded through lumen 36 (FIG. 4A) or slots 36 (FIG. 4B) of pusher tube 26. A distal end of each suture strand is drawn out the distal end of the sheath 24. The suture strands may be of different colors or have different colored patterns—which may correspond to the colors of the suture points on the pouch, so as to allow ease of identification and keep the sutures distinguishable from each other. Next, pusher tube 26 is passed into the sheath 24 such that its distal end faces the folded pouch 12.

Figure 6:
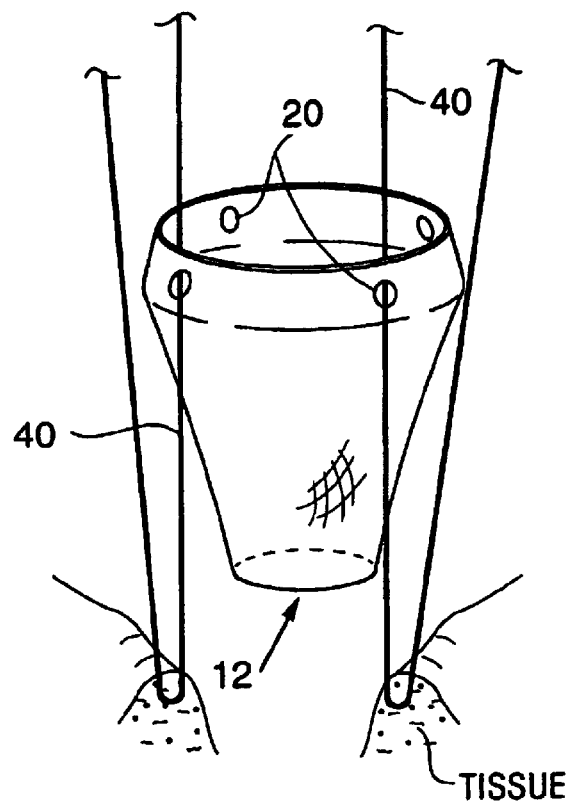
FIG. 6 further illustrates delivery of a pouch into the gastro-esophageal junction. The delivery system is not shown to allow the pouch and sutures to be seen more easily.

The distal end of sheath 24 is passed through the esophagus and into the stomach. The free distal ends of the suture strands 40 are sewn through the tissue surrounding the esophageal opening, preferably just below the Z line. The sutures may be attached under endoscopic guidance if desired, using conventional suturing techniques. See FIGS. 5 and 6. The sheath 24 is not shown in FIG. 6 so that the funnel and sutures can more clearly be shown.

Figure 7:
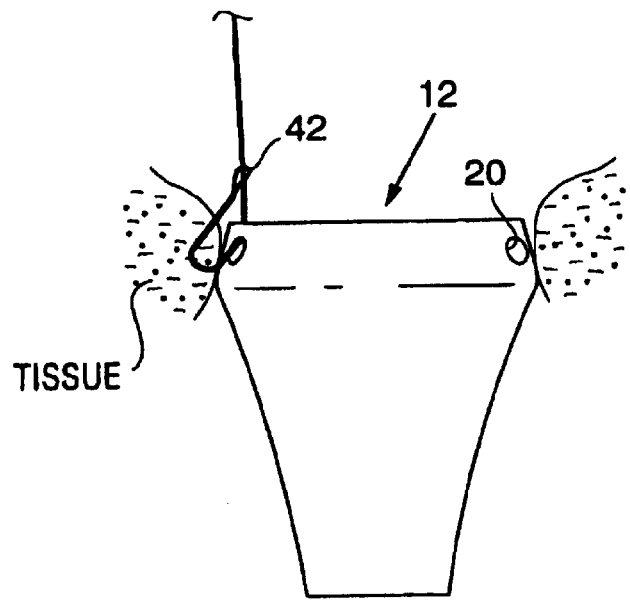
FIG. 7 illustrates final positioning of the pouch of FIG. 6.

Once the sutures have been secured to the tissue, the pusher tube 26 is advanced in a distal direction using handle 30. Pusher tube 26 drives the pouch 12 out the distal opening of the sheath 24. The sheath 24 is positioned with the eyelets 20 at the suture location as shown in FIG. 7. A knot 42 is tied in each suture and slid down the length of the sutures to the tissue, thereby fastening the pouch in place.

Once implanted, the pouch limits passage of food from the patient's esophagus into the stomach. It is believed that as food collects and backs up in the reservoir of the pouch, baroreceptors in the fundus of the stomach and in the gastro-esophageal junction region will trigger a feeling of satiation. Gravity and columnar force will propel food through the reservoir's restricted orifice and into the stomach where normal digestion will occur.

Figure 8:
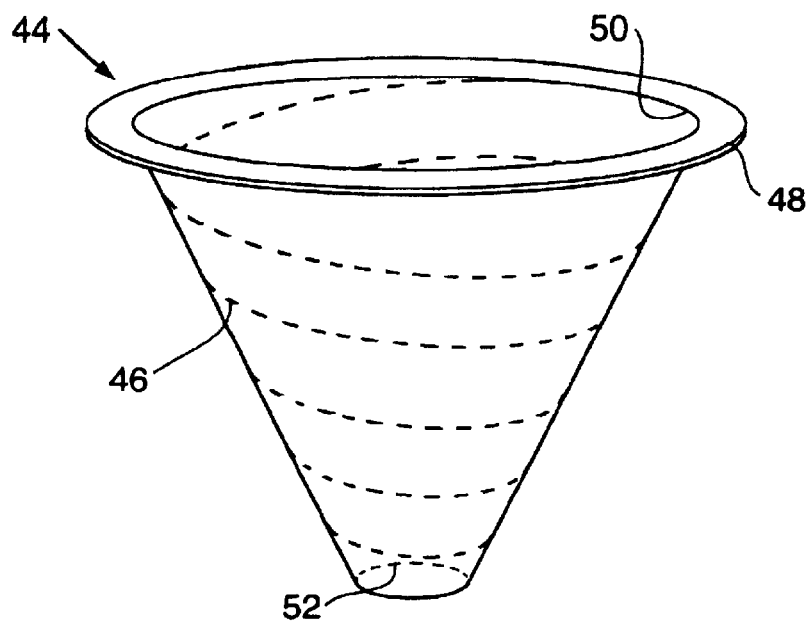
FIG. 8 is a perspective view of an alternative pouch which uses a sewing ring.

FIG. 8 shows a second embodiment of a pouch 44. Pouch 44 includes an elastomeric or semi-compliant material (such as, for example, a durable polyurethane elastomer such as ChronoFlex® polyurethane, silicone, ePTFE mesh or fabric, Dacron® mesh or fabric). The pouch may alternatively be formed of a composite of compliant (or semi-compliant) and non-compliant materials so as to incorporate regions of varying compliance into the pouch. Pouch 44 may include a reinforcing structure such as a helical rib or ring 46—which may be formed of nitinol, stainless steel, plastic etc. The reinforcing structure may be molded or sewn into the pouch material, or it may be attached using a suitable adhesive. A sewing ring 48, which may or may not include eyelets, is circumferentially formed around proximal opening 50. As with all of the embodiments shown, the pouch may taper inwardly towards distal opening 52 to form a funnel shape—or the pouch may have one of a variety of other shapes as discussed previously.

Figure 9A:
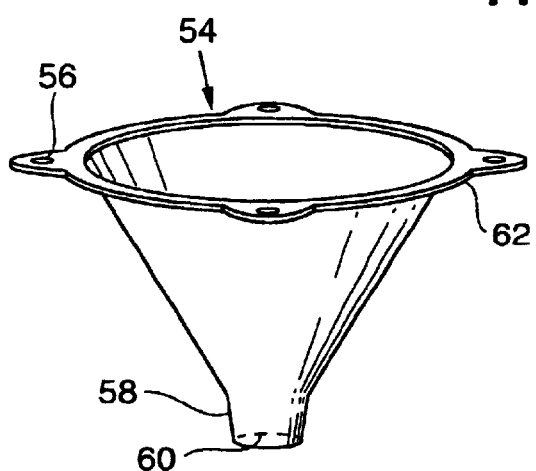
FIGS. 9A and 9B are a perspective view and a top plan view, respectively, of an alternative pouch using a sewing ring.
Figure 9B:
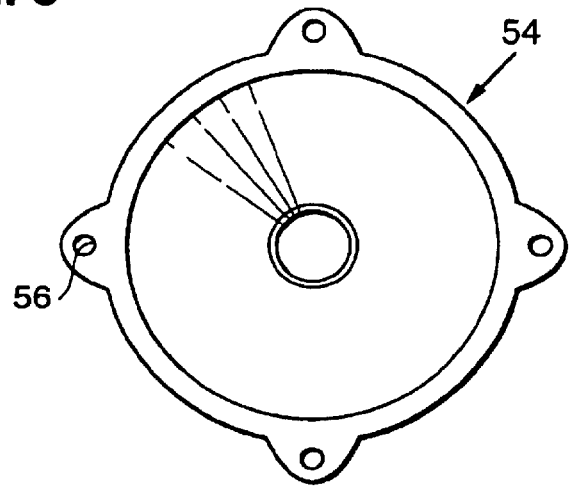
Figure 10:
FIG. 10 is yet another alternative embodiment of a pouch utilizing a sewing ring, and illustrates an alternative pouch shape.

A third pouch 54 is shown in FIGS. 9A and 9B. Pouch 54 is similar to the pouch of FIG. 8 but further includes eyelets 56 in sewing ring 62, and a slightly cylindrical chute 58 adjacent to the distal opening 60. A fourth pouch 63, shown in FIG. 10, also includes a sewing ring 62a, but differs in that its overall shape is shallower and less funnel-shaped.

Figure 11:
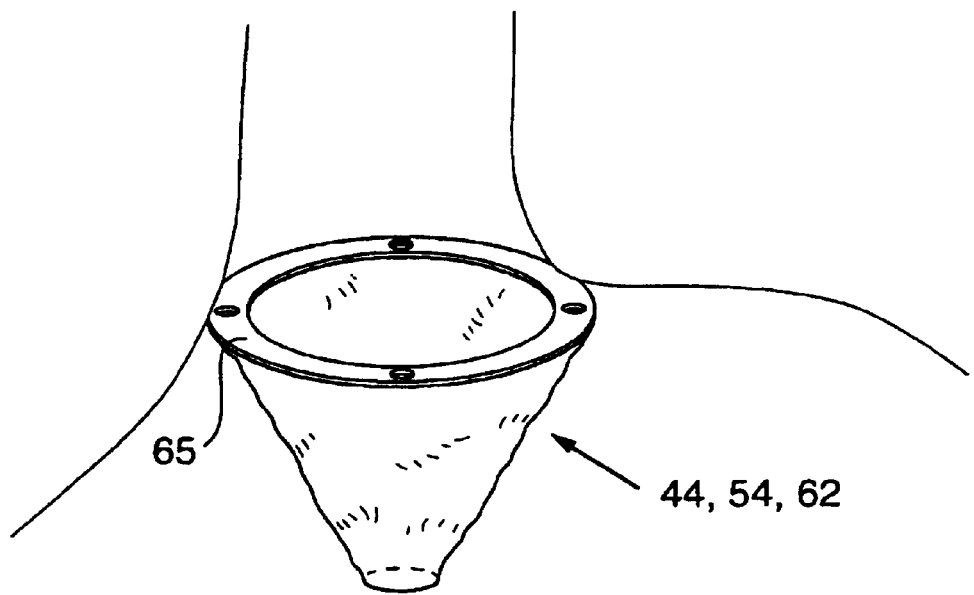
FIG. 11 is a schematic illustration showing positioning of a pouch utilizing a sewing ring as positioned at the gastro-esophageal junction.
Figure 12:
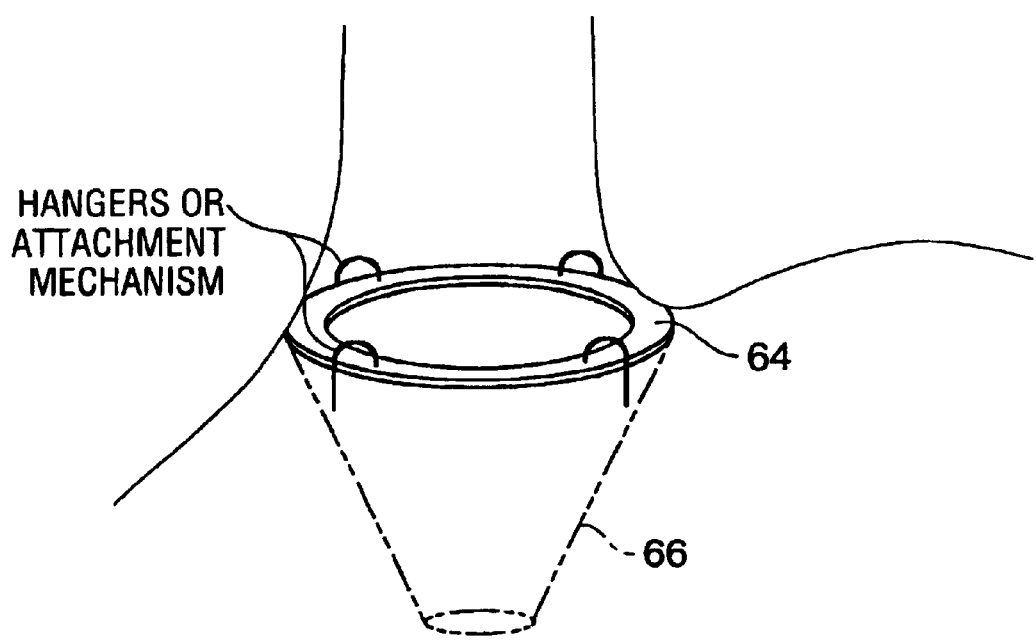
FIG. 12 is a schematic illustration, similar to FIG. 11, showing an alternative pouch which includes a separately implantable sewing ring.

As shown in FIG. 11, a pouch utilizing a sewing ring 65 (such as pouch 44 of FIG. 8, pouch 54 of FIG. 9A, or pouch 62 of FIG. 10) is preferably sewn or plicated into place or otherwise attached to tissue at the upper portion of the stomach S. This positioning is desirable so as to avoid suturing to the thinner esophageal tissue. Because the tissue of the stomach wall is thicker than the esophageal tissue, it provides a more desirable suturing surface. Alternatively, as shown in FIG. 12, a sewing ring 64, which may nitinol or polymeric, may be implanted separately from an associated pouch 66, and sewn-in or plicated to the stomach tissue before introduction of the pouch 66. Afterwards, the pouch 66 is introduced and attached to the ring 64 using sutures, clips or other attachment mechanisms.

To facilitate suturing of a pouch such as those described herein, it may be desirable to form pleats in the tissue at the gastro-esophageal junction region using sutures—in a manner similar to the pleating or "cinching" procedure performed as a treatment for gastrointestinal reflux disease. Such tissue pleats are preferably formed in the stomach tissue below the z-line, and extend radially inwardly from the stomach walls by a small amount. These folds are more easily accessed by a suture needle or clips during attachment of the pouch and thus facilitate implantation of a pouch.

Figure 13A:
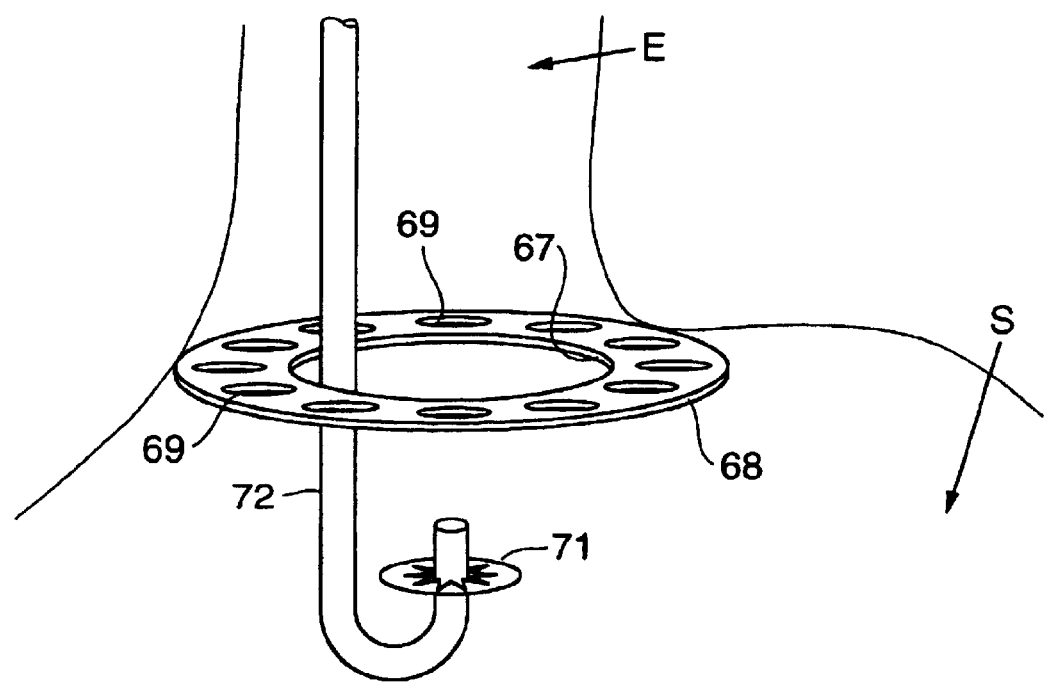
Figure 13B:
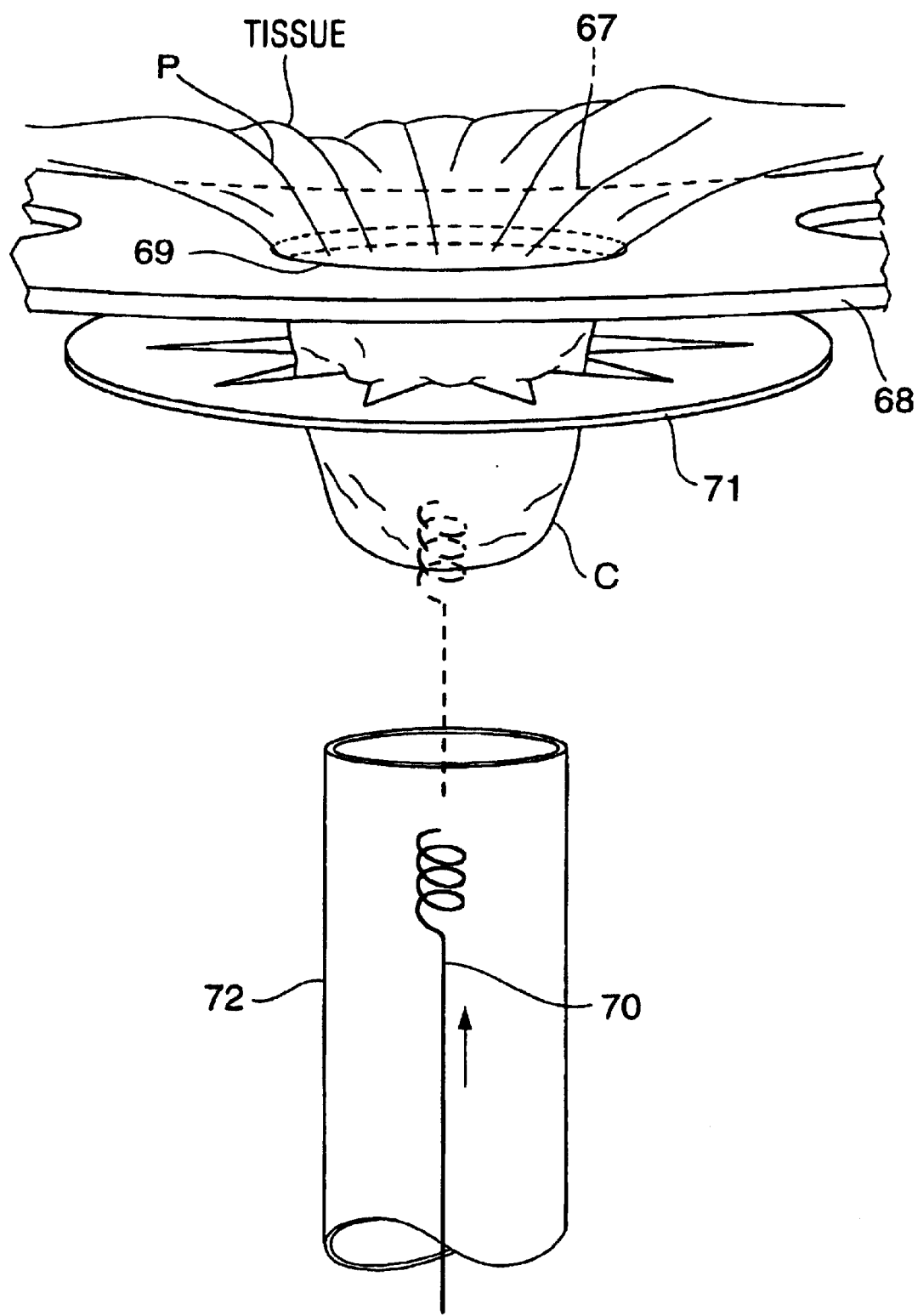

Two alternative mechanisms for forming plications in the stomach tissue are shown in FIGS. 13A, 13B and 14A, 14B. Referring to FIG. 13A, a first plication device includes a ring 68 having a central opening 67 and a plurality of spaced apart circumferential openings 69. Ring 68 is positionable within the proximal stomach as shown (using a sheath to facilitate insertion and placement if desired), such that its circumferential openings 69 are in contact with the stomach tissue surrounding the distal opening of the esophagus. A catheter 72 is extendable through central opening 67. Referring to FIG. 13B, a tissue puller 70 is longitudinally moveable through the catheter. Tissue puller 70 may take the form of an elongate wire having a helical tip—but may alternatively take any other form that will allow it to engage and pull tissue. A flexible locking ring 71 having a central opening shaped to engage tissue pulled through it (e.g. a star-shaped opening) is slidably disposed over the catheter 72 and puller 70.

To plicate tissue at the gastro-esophageal junction region using the device of FIGS. 13A, 13B, ring 68 is positioned against stomach tissue as shown in FIG. 13A. Catheter 72 is passed through central opening 67, and its distal end is steered to a position beneath one of the openings 69 in ring 68. Referring to FIG. 13B, the puller 70 is advanced through opening 69 until it engages the stomach tissue above the ring 68, and the engaged stomach tissue is then pulled through the opening 69 by retracting the puller 70 from the opening 69. A vacuum may be applied through the catheter 72 to assist in the pulling of tissue through the opening 69. Traction is maintained on the puller as locking ring 71 is advanced over the catheter 72 and puller 70, and further advanced over the cone C of tissue drawn through the opening 69—causing the cone of tissue to extend through the star-shaped opening in the locking ring and thereby forming a plication. The locking ring maintains the plication by locking against the tissue due to the points formed by the star-shaped opening. Additional barbs or hooks may be used to facilitate locking. This procedure may be used at some or all of the remaining openings 69 in the ring 68 to attach multiple locking rings 71 to stomach tissue around the perimeter of the esophagus—so as to form plications surrounding the esophagus. A pouch such as those described herein may then be sewn to the plications, or attached to the ring 68 using sutures, clips, adhesives or other suitable means.

Figure 14A:
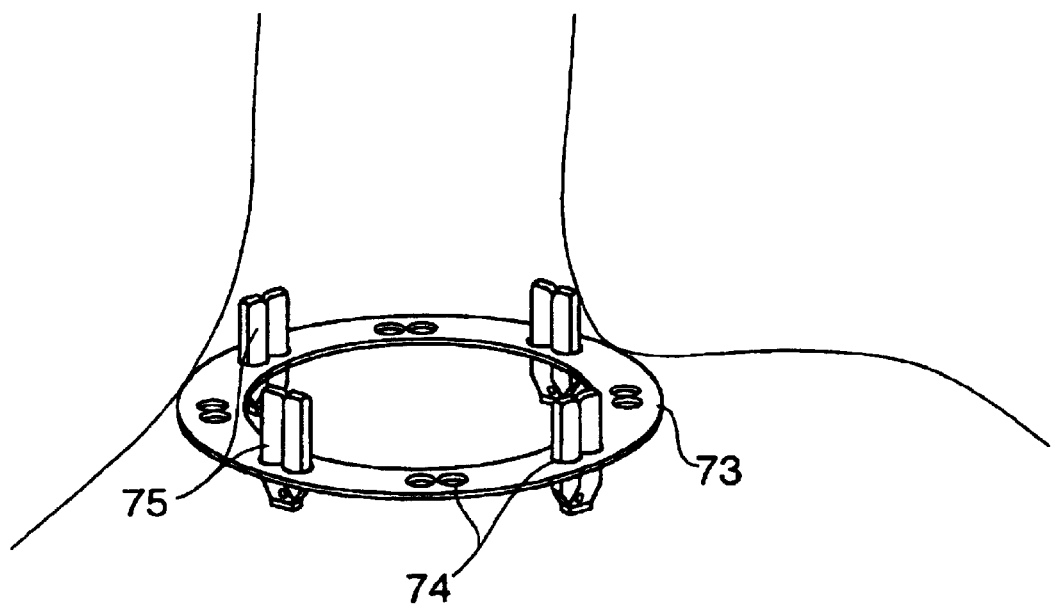
FIG. 14A is a schematic illustration showing an alternative plication device.
Figure 14B:
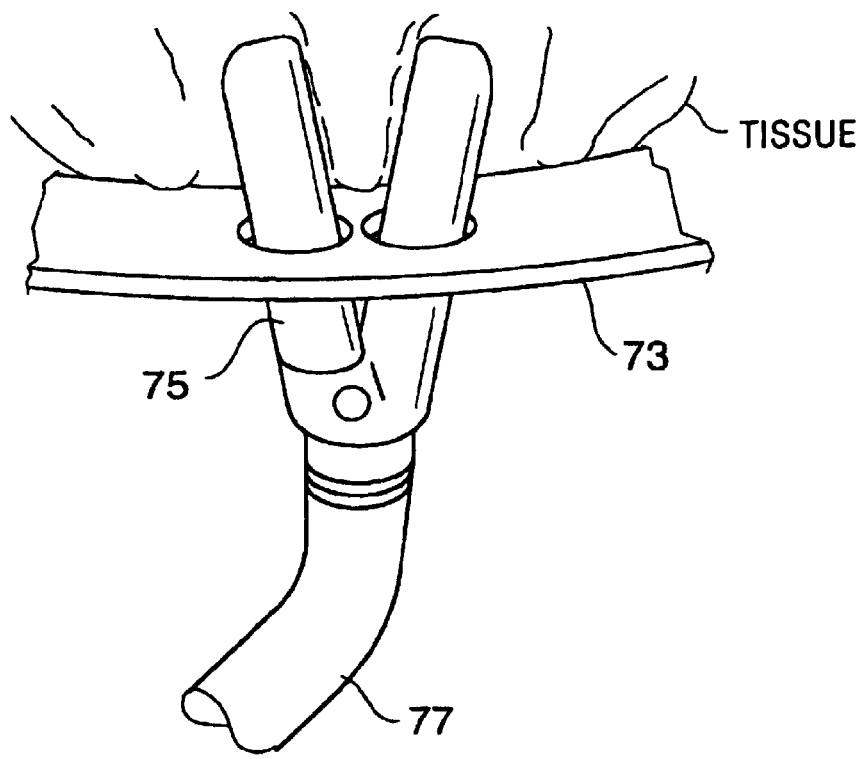
FIG. 14B is a perspective view showing plication of tissue using the device of FIG. 14A.

Another plication device is shown in FIGS. 14A and 14B and includes an annular ring 73 having a plurality of circumferential openings 74. Ring 73 may be formed of an elastomeric material. A plurality of plicating clips 75 include jaw members that extend through adjacent openings 74 in the ring 73 as shown in FIG. 14B. Detachable actuators 77 are provided for opening and closing the jaw members of the plicating clips 75. To plicate tissue, ring 73 is positioned at the gastro-esophageal junction region, with its upper surface in contact with the tissue of the proximal stomach, surrounding the opening to the esophagus. The jaw members of the plicating clips are passed through the openings 74 and used to grasp tissue as shown in FIG. 14B—thereby forming plications in the tissue and holding the ring in place. The jaw members are closed, and locked in the closed position with the grasped tissue between them. The actuators 77 are detached from the clips, leaving the ring and clips in place so as to maintain the plications in the tissue. A satiation pouch may then be sutured to the plications in the tissue as described in connection with the various embodiments described herein, or attached to the ring 73 using sutures, clips, adhesives or other suitable attachment means.

Figure 15:
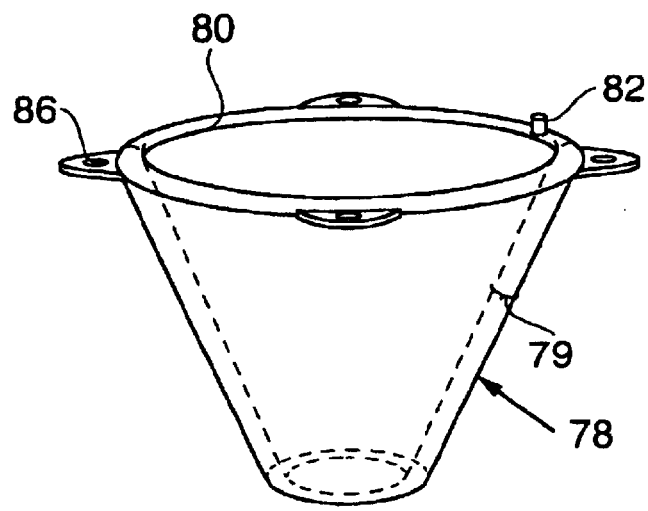
FIG. 15 is a perspective view of an inflatable pouch.
Figure 16:
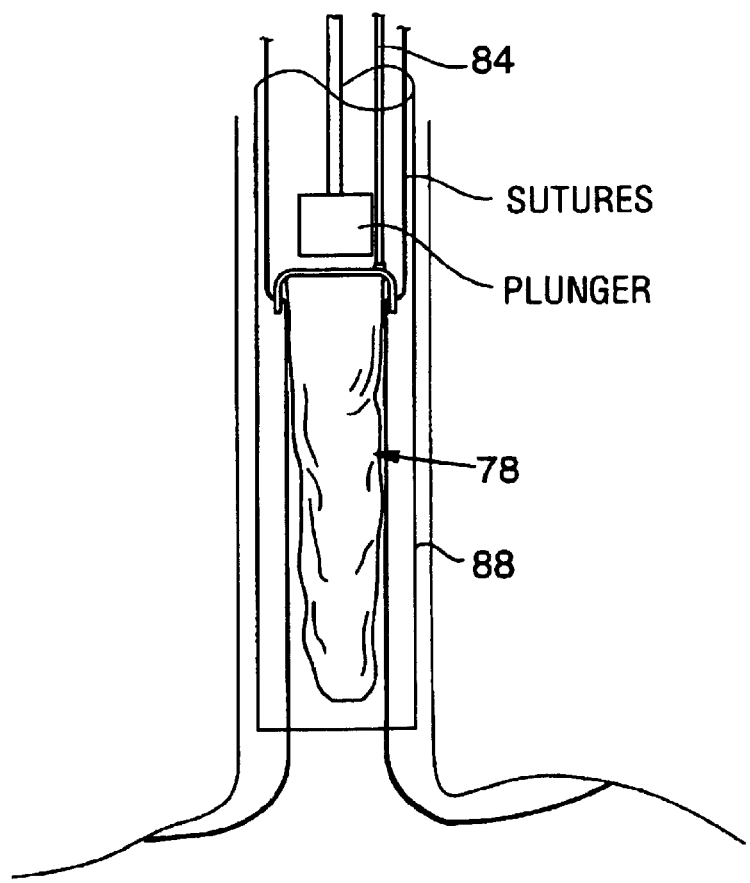
FIG. 16 is a schematic illustration showing delivery of the pouch of FIG. 15 using a delivery device.

FIGS. 15 and 16 show an embodiment of a pouch 78, which differs from prior embodiments in that it is formed as an inflatable cup having an air chamber 79, an inflation valve 82 near the proximal opening 80 and a detachable inflation tube 84. Sewing eyelets 86 surround the proximal opening. After the pouch 78 is deployed into the stomach from a deployment sheath 88 (see FIG. 16), it is inflated by injecting inflation medium (e.g. air or saline) from a syringe into inflation tube 84, and the valve 82 and tube 84 are disconnected from the pouch. When removal of the pouch is desired, the pouch 78 is pierced and deflated, and then pulled through the esophagus using an endoscopic grabber or similar tool.

Referring to FIGS. 17, 18A, and 18B, pouch 90 is formed of rings 92 formed of self-expanding material such as stainless steel, nitinol, or shape memory polymer, covered with a material such as Dacron® polyester, ePTFE fabric, or other polymer that will be durable when sutured to adjacent body tissue. Rings 92 are optionally linked together by ribs 94, which also may be formed of shape memory material.

The distal end of pouch 90 tapers into a chute 96. Chute 96 may be formed of a material similar to that of the pouch, or it may be formed of an elastic polymer, such as a low durometer polyethylene, silicone, elastic polyurethane materials etc. that permits radial expansion of the chute. Such expansion in response to a buildup of food material bearing against the chute may be desirable so as to prevent blockages in the chute. The chute 96 may be collapsible and thereby function as a check valve—preventing reflux of material from the stomach back into the pouch.

An annular sewing region 98 is positioned at the proximal end of the pouch. During implantation, sutures are connected to the sewing region and secured to adjacent tissue. To facilitate suturing of the pouch in place, it may be desirable to form tissue pleats at the gastro-esophageal junction region using sutures—in a manner similar to the pleating or "cinching" procedure performed as a treatment for gastro-intestinal reflux disease. Such tissue pleats extend radially inwardly from the stomach walls by a small amount, and thus can be easily accessed by a suture needle or clips during attachment of the pouch.

Pouch 90 may be provided with a delivery system that includes an elongate mandrel 100 extending through the pouch 90. A nose cone 102 is attached to the distal end of the mandrel, and includes a guidewire 104. Nose cone 102 is preferably flexible and free of sharp or blunt edges so as to prevent tissue trauma during implantation.

As shown in FIG. 18A, pouch 90 is folded and packaged within a positioning sheath 106 formed of a polymer such as a wire reinforced pebax, FEP, ePTFE, or other suitable material. The pouch is folded around the mandrel, and then the folded pouch and mandrel are positioned within the sheath. Various folding techniques may be employed for this purpose. The folded pouch may include bi-directional folds, or overlapping folds. Examples of such folds include propeller folds, rabbit ear folds, saddle folds or cloverleaf folds.

When the pouch is to be implanted, the sheath 106 (with the pouch inside) is introduced into the esophagus, with the guidewire 104 passing first through the esophagus and into the stomach. Once the sewing region 98 has reached the gastro-esophageal junction region, sheath 106 is withdrawn, causing the pouch to spring to the expanded position shown in FIG. 18B due to the self-expanding properties of rings 92. Slight tension is applied to the central mandrel as indicated by arrows in FIG. 18B, so as to cause the sewing region 98 to bear against the tissue encircling the distal opening of the esophagus—or against the pleats formed in the tissue as described above. With the sewing region 98 held against the tissue in this manner, sutures are passed through the sewing region and surrounding tissue so as to secure the pouch into the position shown in FIG. 17. Once the pouch has been sewn into place, the mandrel is withdrawn from the patient, leaving only the pouch in place. After suturing, the mandrel is pushed forward into the stomach where the stretchable nose cone collapses to a diameter smaller than the distal opening of the funnel, and is removed back out through the funnel and esophagus.

Figure 19:
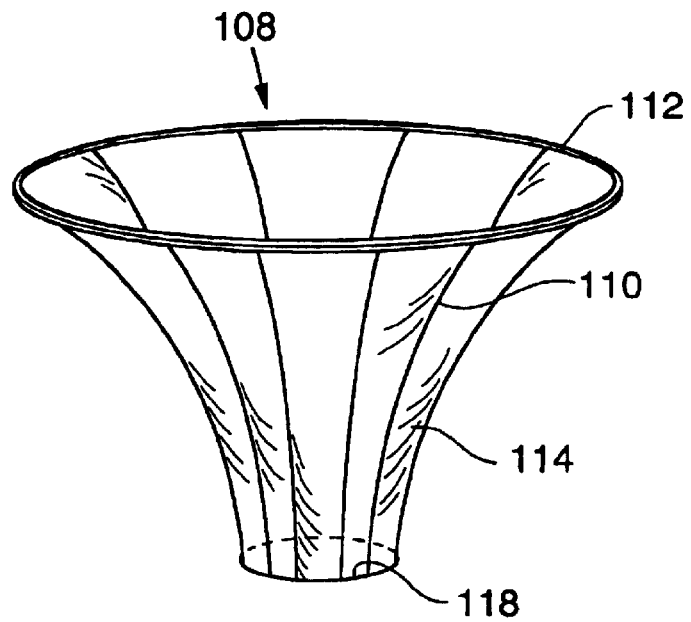
FIG. 19 is a perspective view of yet another embodiment of a stomach pouch.

Referring to FIG. 19 an alternative pouch 108 may be formed of struts 110 or a mesh formed of nitinol, stainless steel, polymer (including shape memory polymer). A ring 112 is attached to the struts/mesh at the proximal end of the device, and also may be formed of nitinol, stainless steel, polymer (including shape memory polymer). The exterior or interior of the pouch covered with a material 114 that will prevent passage of food through the sides of the pouch. One example of such a material is a polyester material such Dacron®polyester sold by the DuPont Company.

Figure 20A:
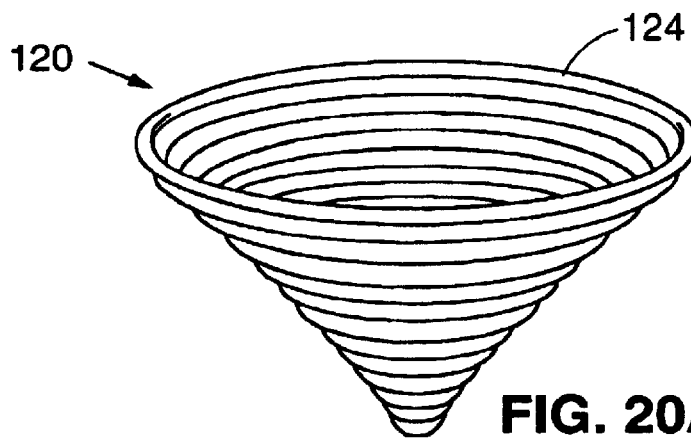
FIG. 20A is a perspective view of yet another alternative stomach pouch, which utilizes a coil configuration.
Figure 20B:
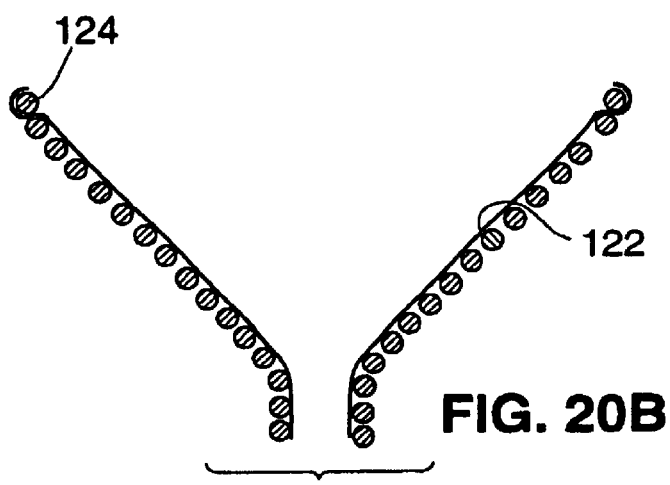
FIG. 20B is a cross-sectional side view of the stomach pouch of FIG. 20A

FIGS. 20A and 20B show another example of a pouch 120. Pouch 120 is formed of a shape memory coil that has been heat set to a funnel shape. Dacron® polyester or other material 122 (FIG. 20B) may optionally cover the interior or exterior walls of the coil, although the coil may itself be sufficiently small as to prevent migration of food through the sidewalls of the coil. The material 122 may be pinched between proximal-most coil 124 and its adjacent coil as shown in FIG. 20B, so as to hold it in place.

Figure 21A:
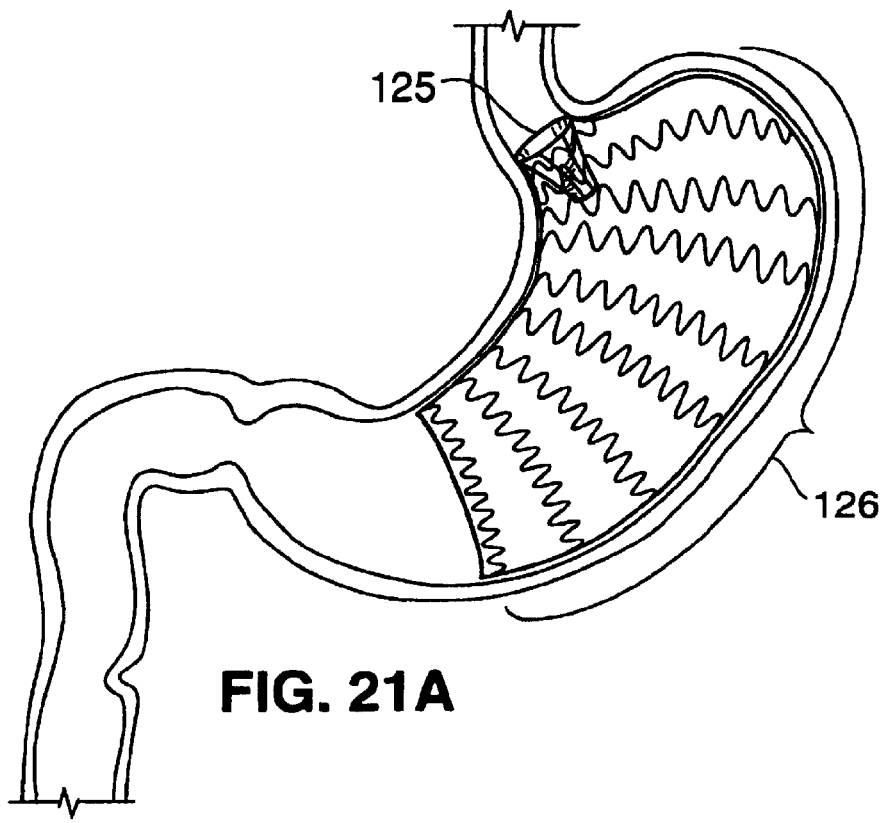
FIG. 21A is a schematic illustration illustrating a fundal cage in combination with a stomach pouch.

As with the other pouches described herein, pouches 108, 120 of FIGS. 19–20B may be provided with a proximal-to-distal dimension that is fairly long (e.g. on the order of approximately 1.5–5.0 cm) and that thus gives the pouch a funnel shape as shown in FIGS. 19 and 20A. However, a variety of alternative shapes may be used for the pouch. For example, the pouch may have a much shorter proximal-to-distal dimension and thus take the shape of a shallow saucer with a small hole on its bottom surface A stomach pouch may alternatively be one portion of a larger satiation device. For example, referring to FIG. 21A, the proximal portion of a pouch 125 may be connected to the proximal end of a larger cage structure 126. Cage 126 extends from the esophagus to the proximal portion of the antrum A. It may be a large stent-like structure preferably formed of self-expanding material, such as stainless steel or a shape memory material such as nitinol or polymer. Cage 126 functions primarily to distend the stomach to create a feeling of satiety. As shown, the pouch 125 is suspended into the interior of cage 126.

Figure 21B:
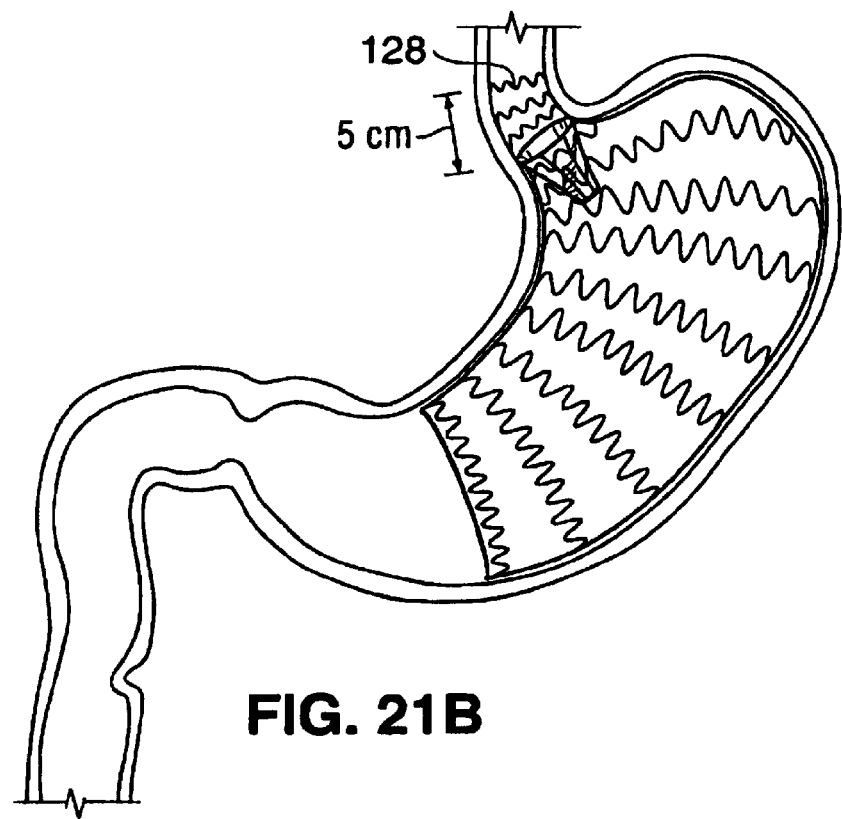
FIG. 21B is a schematic illustration similar to FIG. 21A but further illustrating an alignment extension in combination with the stomach pouch and cage.

Additionally, the pouch 125 (as used with or without cage 126) may also be attached at its proximal end to an alignment extension 128. Referring to FIG. 21B, alignment extension 128 is a tubular stent portion that extends into the esophagus. In one embodiment, extension 128 may be approximately 5 cm in length. It functions primarily to keep the proximal opening of the pouch aligned with the esophagus—so that food passing through the esophagus passes easily into the pouch.

Figure 22A:
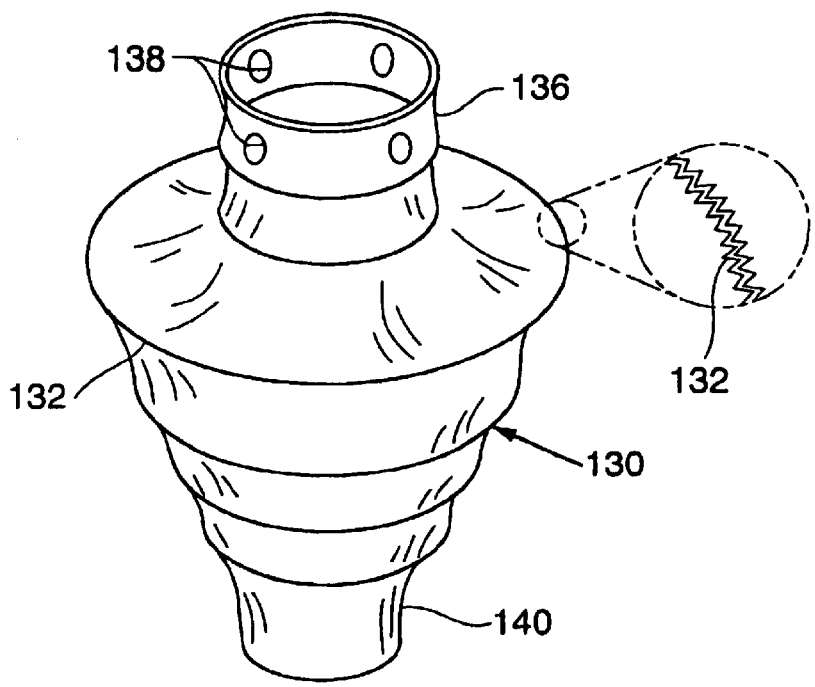
FIG. 22A shows yet another alternative of a stomach pouch embodiment.
Figure 22B:
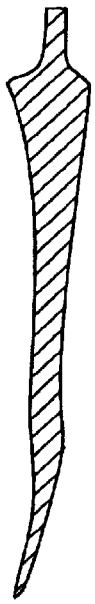
FIG. 22B is a cross-section view of a side-wall of the stomach pouch of FIG. 22A.

Yet another embodiment of a pouch device is shown in FIG. 22A. Pouch 130 is preferably formed of silicone material. The cross-sectional thickness of the pouch wall may differ in different regions of the pouch, so as to allow/limit expansion of the pouch in various locations. The silicone or other material may be coated with a lubricious, bio-compatible, chemically inert material, such as paraleyne, to reduce friction on the base material's surface which will help prevent sticking and food build up on the device.

Figure 22C:
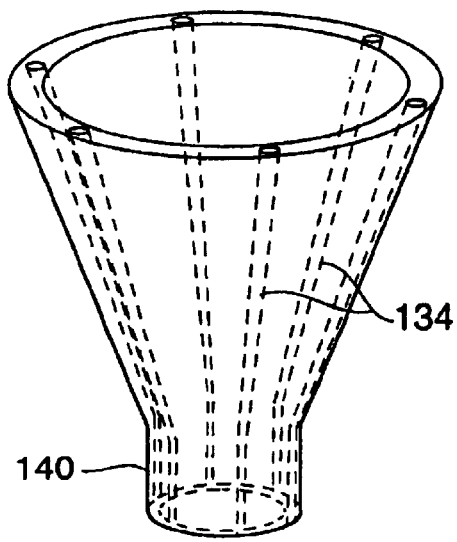
FIG. 22C is a perspective view of a distal chute region of the stomach pouch of FIG. 22A.

Supporting members such as circumferential rings 132 and/or longitudinal ribs 134 (FIG. 22C) may be provided. If provided, such supporting members may be formed of thickened regions of silicone, or they may be separate plastic or nitinol components. As one example, illustrated in FIG. 22A, nitinol rings having an undulating pattern may provide structure to the pouch 130.

A neck 136 is positioned at the proximal end of the pouch 130 and is positionable within the gastro-esophageal junction region. During implantation the neck 136 is secured to the surrounding esophageal tissue and/or stomach tissue using sutures or clips. Suture holes, eyelets or grommets 138 in the neck 136 may be used to provide reinforced regions for anchoring the sutures. In addition, the reinforced locations and materials may be made of a suitably dense radio-opaque material, such as titanium or gold, to add in visualization of the device during or after the procedure. The reinforced locations and material may be of different colors to add in identification and orientation of sutures also. If desired, all or portion of the neck 340 may be formed of a woven material in lieu of silicone so as to provide a more durable sewing region.

Figure 22D:
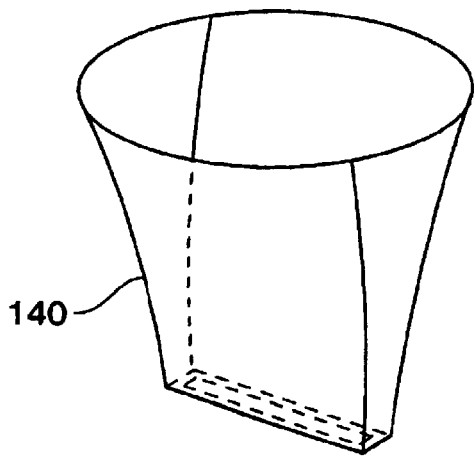
FIG. 22D is a perspective view of a distal chute region alternative to the distal chute region of FIG. 22C.

A chute 140 is formed at the distal end of the pouch 130. Chute 140 may include supporting members such as ribs 134 (or rings such as rings 132) to provide rigidity to the chute. Alternatively, a collapsible chute such as chute 140a shown in FIG. 22D may be utilized. The collapsible chute 140a is provided without rib supports and thus is sufficiently flexible to collapse in response to reflux movement of food material from the stomach into the chute 140a.

Fixation of the funnel device at the gastro-esophageal junction region may also be achieved by using bio-compatible adhesives, thermal fusion, or radio-frequency activated fixation.

The pouch 130, and each of the pouches described herein, may be delivered to the gastro-esophageal junction region using a delivery system such as the one described in connection with FIGS. 3–5, or using other types of delivery systems. An alternative delivery device 142 is shown in FIG. 23. Device 142 includes a plurality of grasper claws 144 extending from an elongate sleeve 146. Claws 144 include a handle 148 that is moveable in a distal direction to distally advance the claws 144 and to simultaneously spread the claws to the opened position shown in FIG. 24A. Movement of the handle 148 in a proximal direction retracts the claws 144 to the closed position shown in FIG. 24B, while simultaneously drawing the claws inside of the sleeve 146.

During use, the delivery device 142 is caused to engage the edge of the pouch (such as pouch 130) at the proximal or distal or end of the pouch. As the claws 144 are closed, they fold the end of the pouch with which they are engaged and draw the pouch towards (or, optionally, into) the sleeve 146. If the claws are used to engage the distal end of the pouch as shown in FIG. 25A, the pouch is preferably turned inside-out before hand, and then folded back over the claws 144 as shown in FIG. 25B to cover the claws. The claws 144, as covered by the pouch 130, are passed through the esophagus and into the stomach to position the pouch, preferably under endoscopic guidance. Once the pouch is within the stomach, the claws 144 are opened to release the pouch. The pouch is positioned in the gastro-esophageal junction region and sutures threaded through the eyelets of the pouch are sewn through neighboring tissue and knotted to secure the pouch in position.

Figure 26:
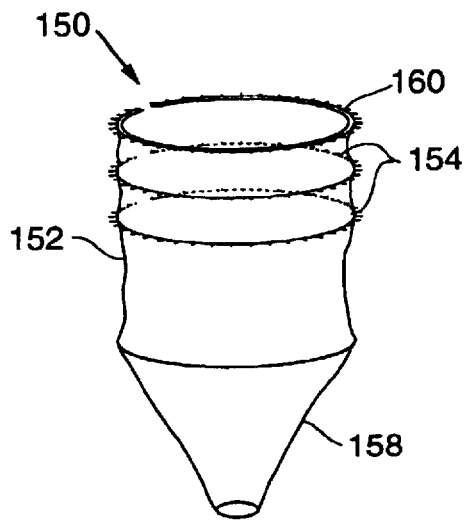
FIG. 26 shows a perspective view of still another stomach pouch.
Figure 27A:
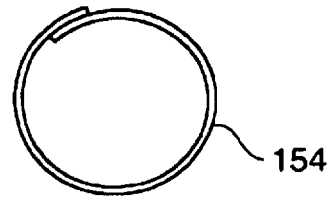
FIGS. 27A and 27B are top plan views showing a ring of the type used in the embodiment of FIG. 26. The ring is shown in the compressed position in FIG. 27A and in the natural, expanded, position in FIG. 27B.
Figure 27B:
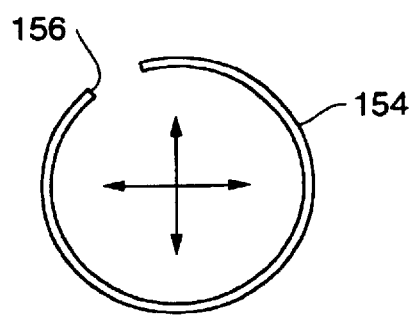

Stomach pouches may alternatively be used as standalone devices without sutures—and may instead be held in place by the radial expansion forces of struts, mesh or coils forming part of the pouch structure. An example of such a pouch 150 is shown in FIG. 26. Pouch 150 includes a neck 152 formed of a flexible polymer, nylon, or Dacron® polyester. A plurality of rings 154 are disposed within this neck. Referring to FIGS. 27A and 27B, each ring 154 includes a break 156 which allows the ring to be radially compressed into the position shown in FIG. 27A—with the ends formed by the break slightly overlapping one another. Release of compression against the ring causes it to spring to the circular position shown in FIG. 27B.

A funnel portion 158 is provided at the distal end of the pouch. As with previous embodiments, when the pouch is implanted the neck 152 is disposed within the gastro-esophageal junction region (e.g. in the distal esophagus as shown) and the funnel portion 158 extends into the stomach.

Prior to implantation, the pouch 150 is preferably packaged within a sheath (not shown) with all of the rings in the compressed position shown in FIG. 27A. Once the neck is placed within the esophagus, the sheath is withdrawn, allowing the rings 154 to spring to the expanded position shown in FIG. 27B. The expanded rings bear against the wall of the esophagus or gastro-esophageal junction region, holding the neck 154 in contact with the wall. Secondary hooks 160 may be optionally provided on the exterior of the neck 154, such that radial expansion of the rings causes the hooks to engage the surrounding walls.

Figure 28A:
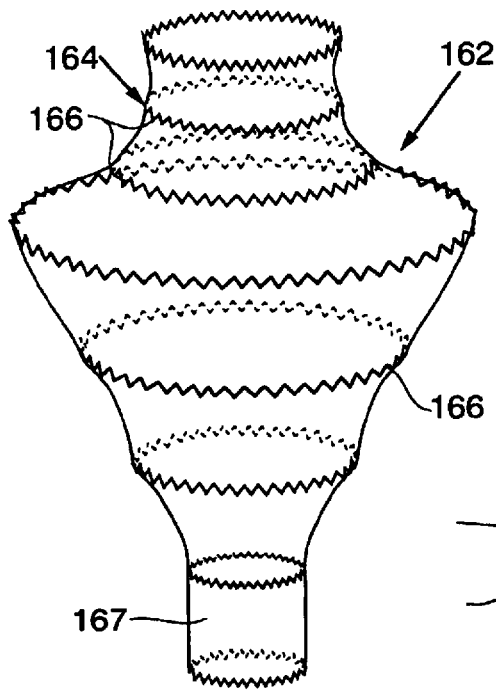
FIG. 28A is a perspective view of still another embodiment of a satiation pouch.
Figure 28B:
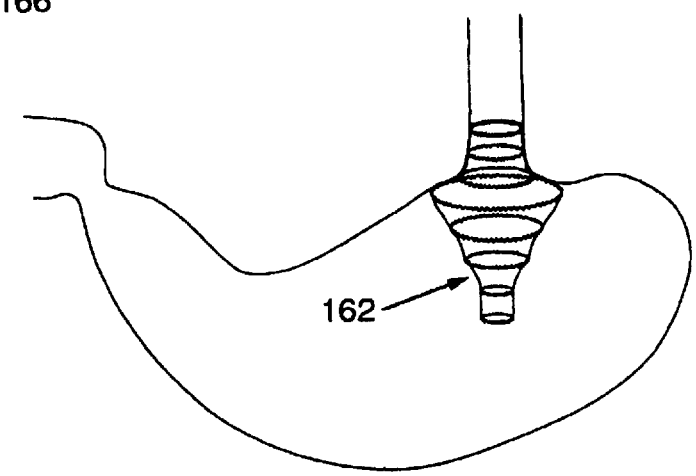
FIG. 28B is a schematic illustration of in vivo positioning of the pouch of FIG. 28A.

FIG. 28A shows an alternative pouch 162 that includes a neck 164 as the sewing region. During implantation, the neck 164 remains within the gastro-esophageal junction region and the distal end of the pouch 162 extends into the stomach. FIG. 28B illustrates that the neck may be secured to esophageal tissue (although as discussed previously it is believed that the tissue below the Z-line may be a more desirable attachment point). Biological adhesives are preferably used to attach the neck and adjacent esophageal tissue to hold the pouch in place. If sutures are used, the self-expanding rings 166 located in the neck may function as suture rings—around which the sutures may be secured. Chute 167 at the distal end may include a duck bill valve which functions as a check valve to control gastro-esophageal reflux.

Figure 29:
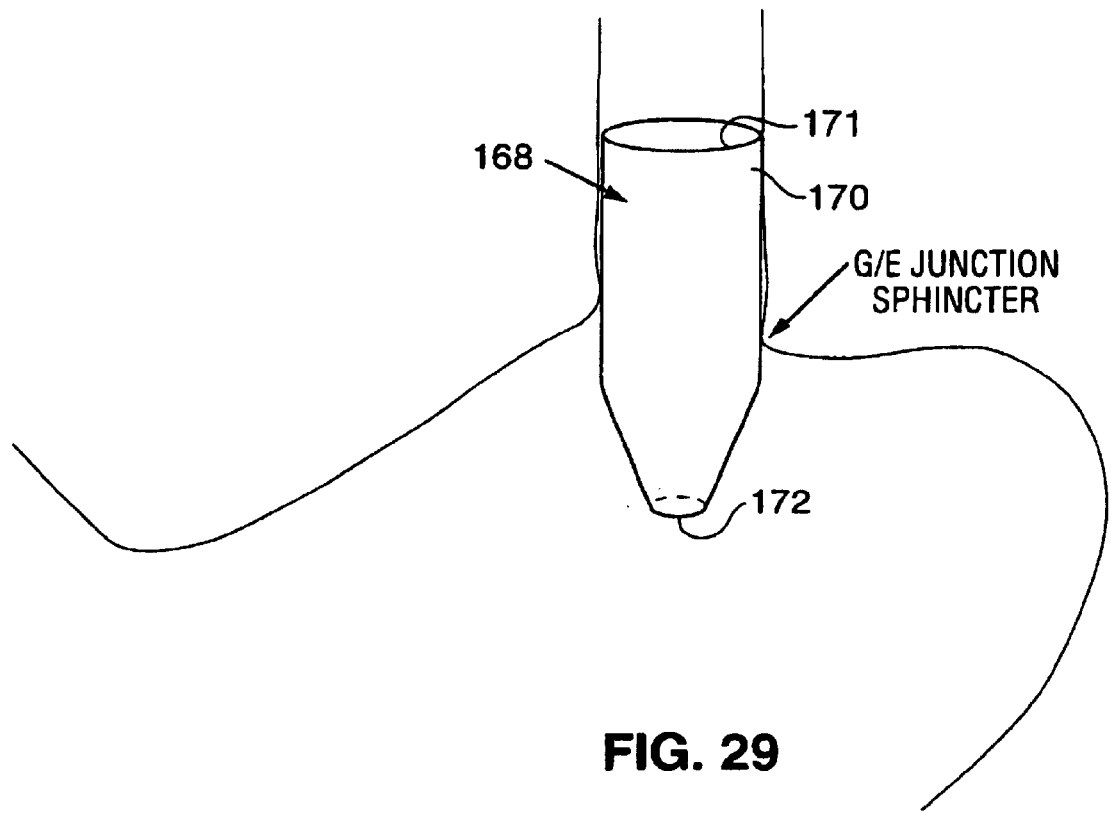
FIG. 29 illustrates in vivo positioning of a trans-esophageal pouch.
Figure 30:
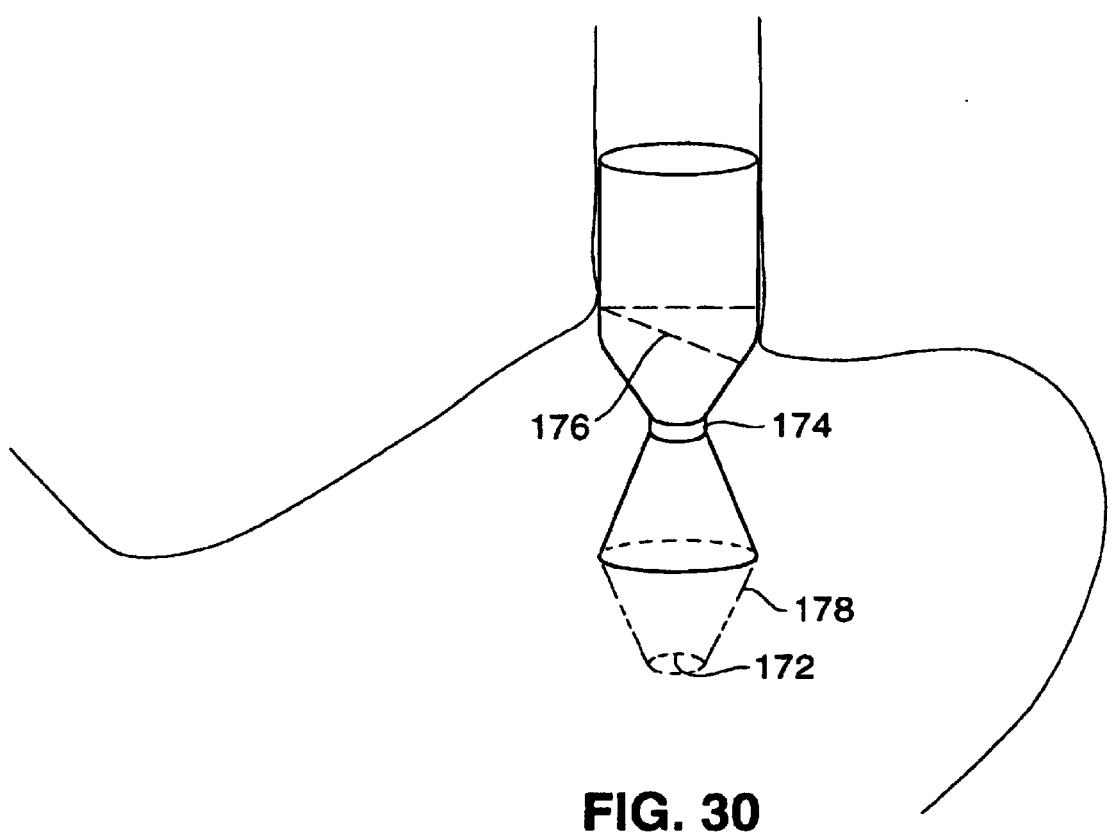
FIG. 30 illustrates in vivo positioning of an alternative trans-esophageal pouch.

Two embodiments of trans-esophageal satiation devices are shown in FIGS. 29 and 30. Referring to FIG. 29, pouch 168 is an elongate flexible device formed of a variably compliant material such as ePTFE, Dacron® polyester, or a polyurethane such as ChronoFlex® polyurethane. Pouch 168 includes a proximal portion 170 positionable within the esophagus and having a proximal opening 171. The pouch further includes an elongate mid-section, and a distal taper that extends into the stomach and that includes a distal opening 172. The flexible nature of the pouch allows for normal function of the esophageal sphincter.

The proximal portion 170 of the pouch (which sits in a proximal position relative to the esophageal sphincter) may include a self-expanding cylindrical stent structure that is formed of shape memory material such as nitinol, shape-memory polymer, or shape-memory alloy and that exerts radial pressure against the surrounding walls so as to hold itself in place within the esophagus. The stent may include barbs in its exterior surface to ensure that the pouch 168 does not move out of place. Alternatively, the proximal portion 172 may instead be attached to the surrounding walls using sutures or barbs. According to this alternative, the pouch may include a stent structure or be provided without.

The embodiment of FIG. 30 differs slightly from the embodiment of FIG. 29 in that it includes an optional tie-wrap restrictor 174 which regulates the rate at which food will move into the stomach from the pouch. The tie-wrap may be adjusted during implantation to select a flow rate appropriate for the patient. Moreover, an optional flapper valve 176 positionable in the vicinity of the esophageal sphincter aids in the prevention of gastro-esophageal reflux. A duckbill valve 178 at the distal opening 172 may also be provided for curtailing gastro-esophageal reflux.

Satiation pouches may be configured to allow the size of the pouch's distal opening to be increased or decreased. This enables a physician implanting such a device to set the distal opening to a size appropriate for a patient. In some cases, it will also allow the physician to make adjustments to the distal opening after it has been implanted. For example, if the patient is not losing weight at a desired rate, the physician might reduce the size of the distal opening—so that food will empty more slowly from the pouch into the stomach. The physician might alternatively increase the size of the distal opening if necessary if weight loss is occurring too rapidly.

Figure 31:
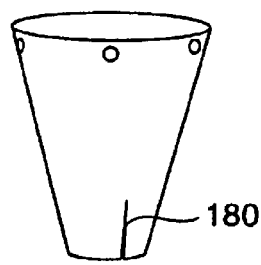
FIG. 31 is a front elevation view of a satiation pouch having an adjustable distal opening.

Referring to FIG. 31, longitudinal cuts 180 may be formed in the distal end of the pouch to increase the effective size of the distal opening. These cuts may be made using endoscopic scissors after the pouch has been implanted, or they may be made prior to implantation. The device may be perforated or scored beforehand to facilitating cutting.

Figure 32A:
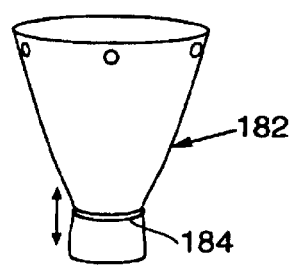
FIG. 32A is a front elevation view of a satiation pouch having an alternative form of adjustable distal opening.
Figure 32B:
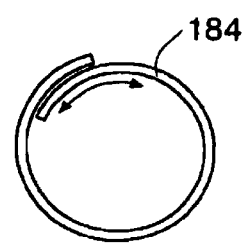
FIG. 32B is a top plan view of the adjustable restrictor ring of the pouch of FIG. 32A.

Referring to FIGS. 32A and 32B, a pouch 182 may alternatively be provided with a restrictor ring 184 surrounding the exterior of the pouch—near the distal opening. Ring 184 may be expanded by applying expansive radial forces from within the inner diameter of the ring (e.g. by positioning the jaws of a grasper within the funnel and then separating the jaws), or compressed using compressive forces applied to the exterior of the ring (e.g. by positioning the ring between the jaws and then closing them slightly). This expansion/compression may be performed prior to implantation, or after the pouch has been implanted.

Figure 33:
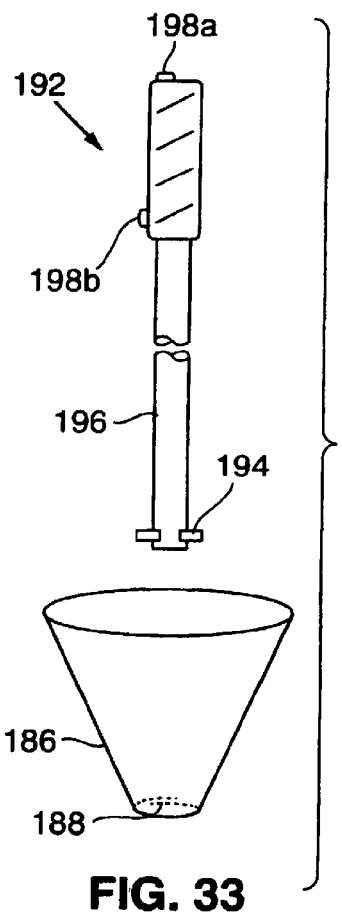
FIG. 33 is a side elevation view of a satiation pouch having yet another form of adjustable distal opening, and a tool useable for adjusting the distal opening.
Figure 34A:
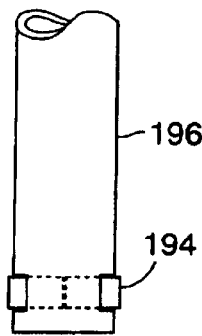
FIGS. 34A and 34B are side elevation views showing the distal end of the tool shown in FIG. 33 in the retracted and expanding positions, respectively.
Figure 34B:
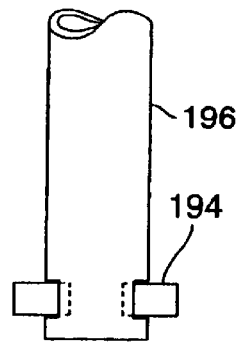
Figure 35A:
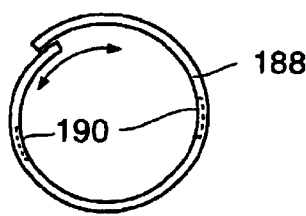
FIGS. 35A and 35B are top plan views of the adjustable restrictor ring of the pouch of FIG. 33, showing the ring in expanded and contracted positions.
Figure 35B:
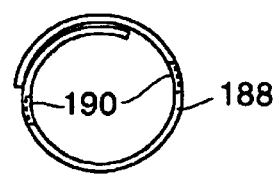

FIG. 33 shows a third alternative embodiment of a pouch 186 having an adjustable distal opening. The FIG. 33 embodiment is similar to the FIG. 32A embodiment in that it relies upon expansion/contraction of a restrictor ring. Restrictor ring 188 is positioned inside the pouch near the distal opening. A pair of opposed slots 190 are formed in the interior surface of the ring 188. An endoscopically-controllable adjustment tool 192 includes a pair of extendable pins 194 at the distal end of an elongate shaft 196. Actuators 198a,b on the proximal end of the adjustment tool 192 control extension of the pins between the retracted position (FIG. 34A) and the extended position (FIG. 34B). To adjust the diameter of the pouch 186, tool is inserted through the pouch with the pins 194 in the retracted position. Pins 194 are aligned with slots 190 in the ring 188 and are then extended using actuators 198a. As they extend, the pins 194 slide into the slots 190. Next, the user rotates the tool 192 about its longitudinal axis, in either the clockwise or counter-clockwise direction. Rotation of the tool expands or contracts the ring, depending on the direction of rotation. After the ring size has been adjusted, the pins 194 are retracted using actuator 198b, and the tool 192 is removed from the pouch 186.

Many techniques may be used to remove a satiation pouch from the stomach. One example is shown in FIGS. 36A–36D. First, if sutures or clips are used, endoscopic scissors 202 are passed through the mouth and esophagus and used to snip the sutures (FIG. 36A) or remove the clips. It may be desirable to engage the pouch 200 using, for example, a leash sewn through the pouch and extending out through the mouth, or an endoscopic grabber etc. to prevent the pouch from falling further into the stomach after it has been detached from the gastro-esophageal junction region.

Figure 36A:
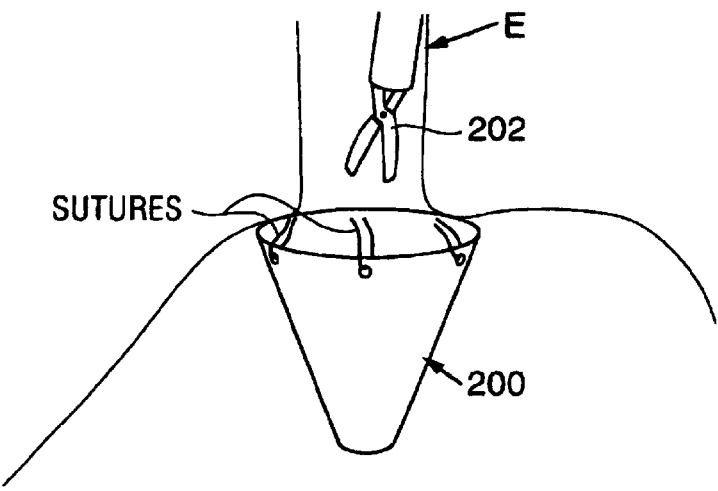
FIGS. 36A through 36D are a series of figures schematically illustrating removal of a satiation pouch from a patient.
Figure 36B:
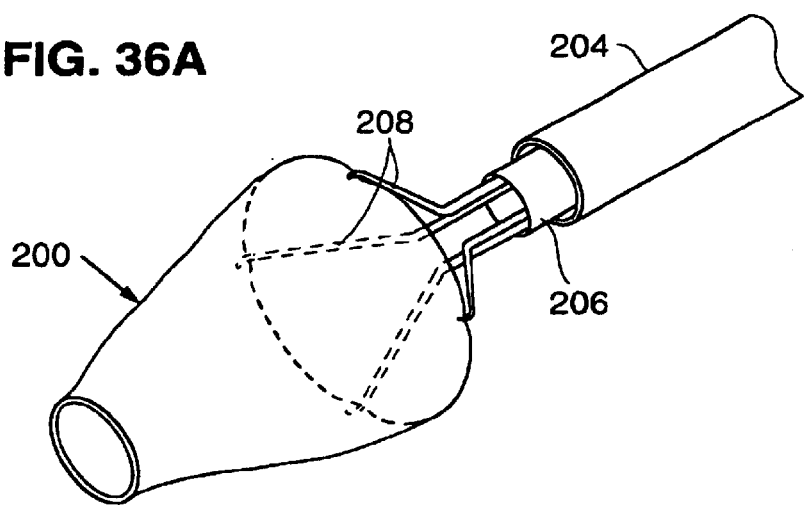
Figure 36C:
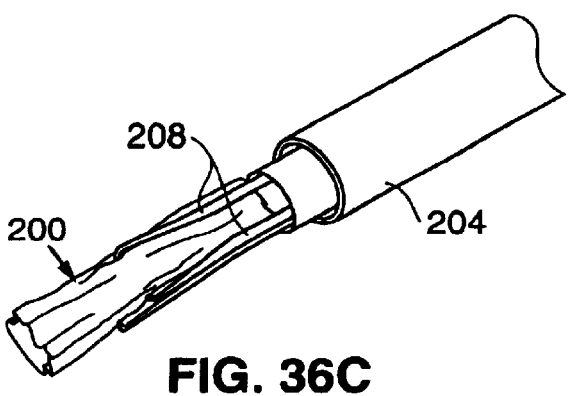
Figure 36D:
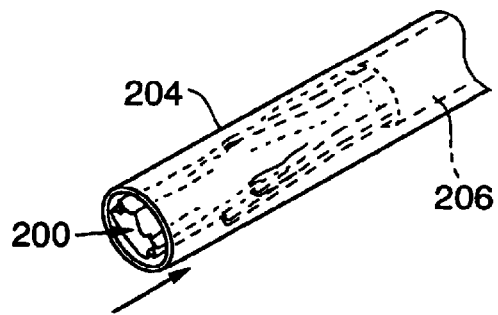
Figure 37:
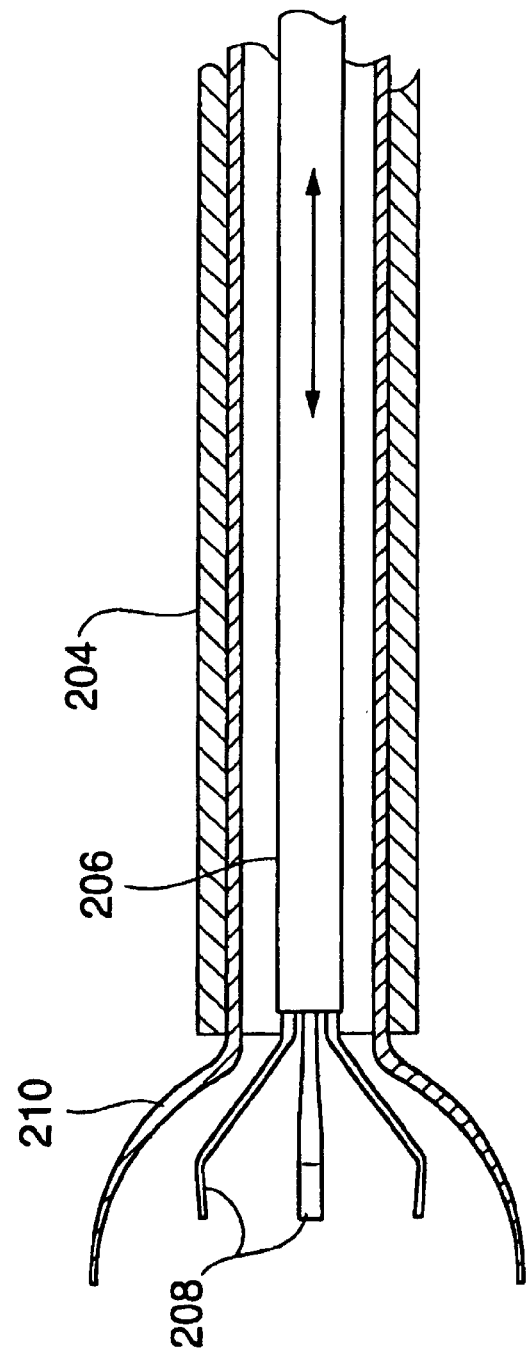
FIG. 37 is a cross-sectional side elevation view of a pouch extraction tool that may be used in combination with the tools shown in FIGS. 36A–36D.

Next, a sheath 204 is passed through the esophagus to the gastro-esophageal junction region. A retrieval device 206 having expandable claws 208 (that may be similar to those of the device of FIG. 23) is positioned with its claws 208 in a closed position, and is passed through the sheath. The claws 208 are opened, positioned around the proximal portion of the pouch 200 (FIG. 36B), and then closed to collapse the pouch between the claws (FIG. 36C). The claws 208 are then withdrawn through the sheath and out of the body to remove the pouch (FIG. 36D). To facilitate removal, a flexible hood 210 having a flared distal end may be extended through the sheath and positioned to extend from the distal end of the sheath (see FIG. 37) during pouch removal. The hood 210 helps guide the pouch into a compressed position as the pouch is drawn into the sheath 204. Once the pouch has been removed, the hood 210 is withdrawn from the body via the sheath 204, and then the sheath is withdrawn.

Figure 38A:
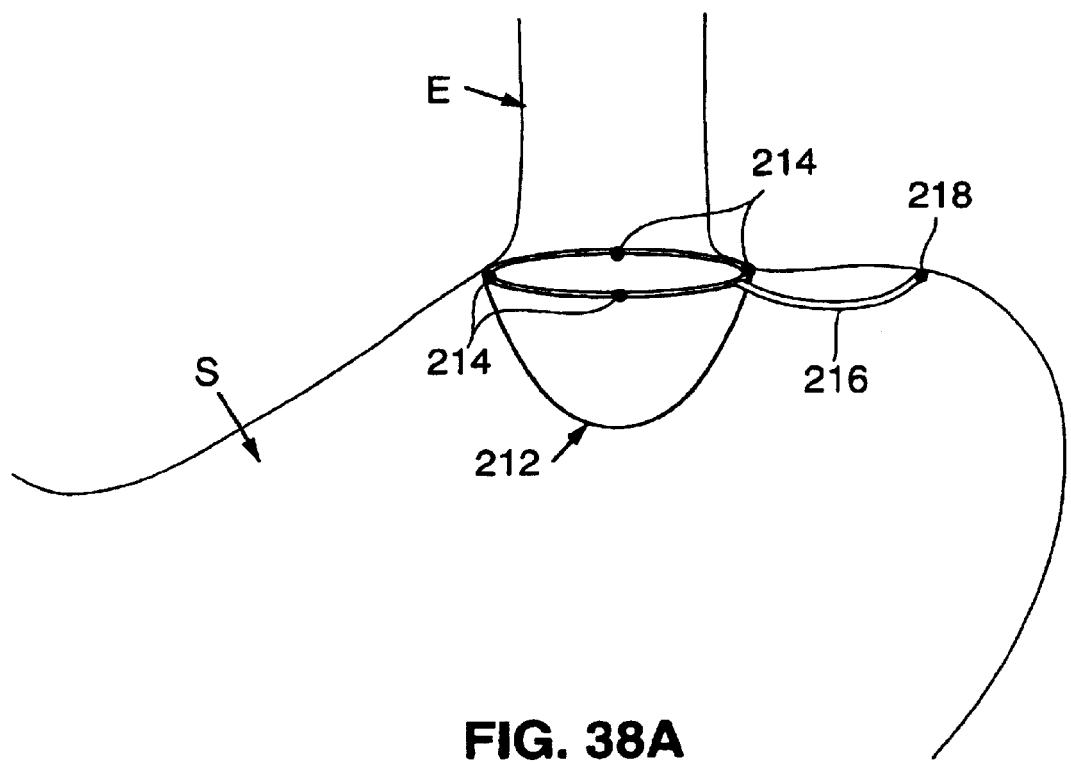
FIGS. 38A and 38B are schematic illustrations of a stomach and esophagus, illustrating a satiation pouch having a safety leash.
Figure 38B:
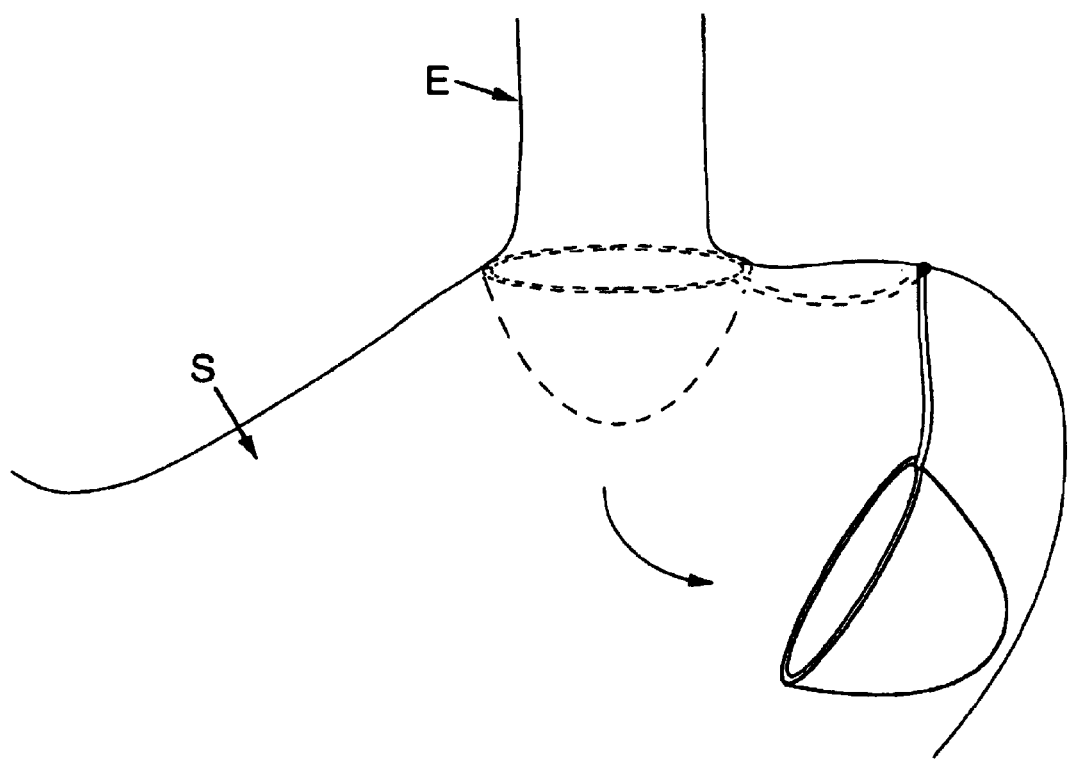

Referring to FIGS. 38A and 38B, a satiation pouch 212 may include a safety leash 216 that will retain the pouch 212 within the proximal region of the stomach in the event of failure of the primary mechanism (e.g. sutures, clips, adhesive, etch) for holding the pouch in position. Leash 216 extends from the pouch and is secured to the stomach wall at point 218. Leash 216 may be constructed using materials of the type used for the pouch, or using fiber reinforced ribbon of such materials. In the example shown in FIGS. 38A and 38B, the proximal portion of pouch 212 is secured in place using sutures at attachment points 214. If these suture connections should fail, the pouch will be retained by the leash, and will be prevented from migrating into the antrum or the pylorus region of the stomach, and will thus prevent an occlusive event.

Various embodiments of satiation device have been described herein. These embodiments are giving by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

We claim:

1. A method for inducing weight loss in patient, comprising the steps of:
    providing a pouch having a proximal opening and a distal opening;
    positioning at least a portion of the pouch within the stomach of a patient;
    retaining the proximal portion of the pouch within the gastro-esophageal junction region such that the proximal opening receives food from the esophagus and such that the distal opening is positioned within the stomach; and
    causing food ingested by the patient to flow from the esophagus to the proximal opening, and out the distal opening into the stomach.

2. The method of claim 1 wherein the proximal opening as a diameter that is larger than the diameter of the distal opening.

3. The method of claim 2 wherein the pouch has an approximate funnel shape.

4. The method of claim 1 wherein the retaining step includes securing the proximal portion to tissue below the Z-line of the gastro-esophageal junction region.

5. The method of claim 1 wherein the retaining step includes securing the proximal portion to tissue above the Z-line of the gastro-esophageal junction region.

6. The method of claim 1 wherein the retaining step includes securing the proximal portion to tissue using sutures.

7. The method of claim 1 wherein the retaining step includes securing the proximal portion to tissue using clips.

8. The method of claim 1 wherein the retaining step includes securing the proximal portion to tissue using biological adhesive.

9. The method of claim 1 wherein the pouch includes a neck and wherein the proximal opening is formed in the neck.

10. The method of claim 9, wherein the retaining step includes securing the neck within the esophagus.

11. The method of claim 1 wherein the pouch is expandable from a collapsed position to an expanded position, and wherein the method includes passing the pouch into the stomach in the collapsed position, and expanding the pouch to the expanded position.

12. The method of claim 11 wherein the pouch is self-expandable from the collapsed to the expanded position.

13. The method of claim 1 wherein the positioning step includes extending a sheath through a patient's esophagus to the gastro-esophageal junction region, and passing the pouch though the sheath and into the stomach.

14. The method of claim 13 wherein the passing step includes pushing the pouch through the sheath using a pushing tool.

15. The method of claim 1 wherein the positioning step includes grasping the pouch using jaw members of a grasper, inserting a sheath through a patient's esophagus to the gastro-esophageal junction region, and carrying the pouch through the sheath and into the stomach using the grasper.

16. The method of claim 1 wherein the distal opening has a diameter and wherein the method includes the step of adjusting the diameter of the distal opening.

17. The method of claim 16 wherein the adjusting step is performed prior to the retaining step.

18. The method of claim 17 wherein the adjusting step is performed after the retaining step.

19. The method of claim 1, further including the step of leaving the pouch within the stomach for a desired period of time, and then removing the pouch from the stomach.

20. The method of claim 19 wherein the removing step includes passing a sheath through the esophagus, grasping the pouch using a grasping device extended through the sheath, and withdrawing the pouch into the sheath.

21. The method of claim 20 wherein the removing step further includes clipping sutures extending between the sheath and the stomach prior to withdrawing the pouch.

22. The method of claim 1 wherein the distal opening limits passage of food from the esophagus into the stomach.

23. The method of claim 1 wherein the retaining step includes the step of forming at least one plication in tissue of the gastro-esophageal junction region, and coupling the pouch to the plication.

24. The method of claim 1 wherein the retaining step includes the step of coupling a ring to tissue of the gastro-esophageal junction region, and coupling the pouch to the ring.

25. The method of claim 1 wherein the retaining step includes the step of forming at least one plication in tissue of the gastro-esophageal junction region, coupling a ring to the plication, and coupling the pouch to the ring.

26. The method of claim 1 wherein the pouch forms a reservoir having a volume of approximately 2–300 cc.

27. The method of claim 1 wherein the pouch forms a reservoir having a volume of approximately 10–30 cc.

* * * * *